United States Patent
Fu et al.

(10) Patent No.: US 7,835,500 B2
(45) Date of Patent: Nov. 16, 2010

(54) MULTI-PHASE REGISTRATION OF 2-D X-RAY IMAGES TO 3-D VOLUME STUDIES

(75) Inventors: Dongshan Fu, Santa Clara, CA (US); Gopinath Kuduvalli, San Jose, CA (US)

(73) Assignee: Accuray Incorporated, Sunnyvale, CA (US)

( * ) Notice: Subject to any disclaimer, the term of this patent is extended or adjusted under 35 U.S.C. 154(b) by 967 days.

(21) Appl. No.: 11/281,106

(22) Filed: Nov. 16, 2005

(65) Prior Publication Data
US 2007/0127845 A1    Jun. 7, 2007

(51) Int. Cl.
*G06K 9/00*    (2006.01)
(52) U.S. Cl. .................... 378/128; 128/922; 378/4
(58) Field of Classification Search ................ 382/294, 382/128, 129, 130, 131, 132, 154, 174, 285, 382/194; 128/922; 378/4–27
See application file for complete search history.

(56) References Cited

U.S. PATENT DOCUMENTS

| | | | |
|---|---|---|---|
| 5,117,829 A | 6/1992 | Miller et al. | |
| 5,901,199 A * | 5/1999 | Murphy et al. | 378/65 |
| 5,954,647 A | 9/1999 | Bova et al. | |
| 6,125,164 A | 9/2000 | Murphy et al. | |
| 6,235,038 B1 | 5/2001 | Hunter et al. | |
| 6,307,914 B1 | 10/2001 | Kunieda et al. | |
| 6,470,207 B1 | 10/2002 | Simon et al. | |
| 6,501,981 B1 | 12/2002 | Schweikard et al. | |
| 6,516,046 B1 | 2/2003 | Frohlich et al. | |
| 6,597,818 B2 * | 7/2003 | Kumar et al. | 382/294 |
| 6,665,555 B2 | 12/2003 | Henderson et al. | |
| 6,782,287 B2 * | 8/2004 | Grzeszczuk et al. | 600/424 |
| 6,907,281 B2 * | 6/2005 | Grzeszczuk | 600/407 |
| 7,024,237 B1 | 4/2006 | Bova et al. | |
| 7,171,257 B2 | 1/2007 | Thomson | |
| 7,187,792 B2 | 3/2007 | Fu et al. | |
| 7,204,640 B2 * | 4/2007 | Fu et al. | 378/205 |
| 7,302,033 B2 * | 11/2007 | Carrano et al. | 378/41 |
| 7,327,865 B2 | 2/2008 | Fu et al. | |
| 7,480,399 B2 | 1/2009 | Fu et al. | |
| 7,522,779 B2 * | 4/2009 | Fu et al. | 382/254 |
| 2002/0077543 A1 | 6/2002 | Grzeszczuk et al. | |
| 2004/0092815 A1 | 5/2004 | Schweikard et al. | |
| 2004/0131150 A1 | 7/2004 | Pankratov et al. | |
| 2004/0267113 A1 | 12/2004 | Thomson | |

(Continued)

OTHER PUBLICATIONS

Gustafsson, Adaptive Filtering and Change Detection, 2001, Wiley, ISBN: 9780471492870 Online ISBN: 9780470841617, p. 126.*

(Continued)

*Primary Examiner*—Anand Bhatnagar
(74) *Attorney, Agent, or Firm*—Blakely, Sokoloff Taylor & Zafman LLP

(57) ABSTRACT

A method for registering 2-D radiographic images to 3-D volume studies includes generating digitally reconstructed radiographs (DRRs) from a 3-D volume study. The DRR's are used as reference images to register a patient's position during image-guided radiosurgery. Stereoscopic X-rays of the patient are acquired during treatment, and multi-phase registration is used to register the DRRs with the X-ray images in two or more projections.

51 Claims, 13 Drawing Sheets

U.S. PATENT DOCUMENTS

| | | | |
|---|---|---|---|
| 2005/0047544 A1* | 3/2005 | Fu et al. | 378/63 |
| 2005/0049477 A1 | 3/2005 | Fu et al. | |
| 2005/0049478 A1* | 3/2005 | Kuduvalli et al. | 600/407 |
| 2005/0249398 A1* | 11/2005 | Khamene et al. | 382/154 |
| 2007/0003123 A1* | 1/2007 | Fu et al. | 382/131 |
| 2007/0110289 A1* | 5/2007 | Fu et al. | 382/128 |

OTHER PUBLICATIONS

Dongshan Fu et al., "Automated Skull Tracking for the CyberKnife Image-guided Radiosurgery System", Proceedings of SPIE on CD-ROM, Medical Imaging 2005, Feb. 12-17, 2005, San Diego, California, USA, vols. 5744-5750, Medical Imaging 2005: Visualization, Image-Guided Procedures, and Display, pp. 366-377.

Coste-Manière, È., "Robotic whole body stereotactic radiosurgery: clinical advantages of the CyberKnife® integrated system", The International Journal of Medical Robotics+Computer Assisted Surgery, 2005, www.roboticpublications.com, pp. 28-39.

International Search Report, International Application No. PCT/US04/27158, International filing date Aug. 20, 2004, mailed Sep. 6, 2005, 16 pages.

Maintz, J.B.A., et al., A survey of medical image registration, Medical Image Analysis, vol. 2, 1998, pp. 1-37.

Murphy, Martin J., "An automatic six-degree-of-freedom image registration algorithm for image-guided frameless sterotaxic radiosurgery," Med. Phys. 24(6), 857-866, Jun. 1997.

Penney, Graeme P., et al., "Validation of a two- to three-dimensional registration algorithm for aligning preoperative CT images and intraoperative fluoroscopy images," Med. Phys. 28(6), 1024-1032, Jun. 2001.

Sarrut, D., et al., "Patient positioning in radiotherapy by registration of 2D portal to 3D CT images by a contend-based research with similarity measures," Cars 2000, 707-712.

Bifulco, Paolo, et al., Estimation of out-of-plane vertebra rotations on radiographic projections using CT data: a simulation study, Medical Engineering and Physics 24 (2002), pp. 295-300.

International Report on Patentability, International Application No. PCT/US04/27158, International filing date Aug. 20, 2004, mailed Feb. 9, 2006, 10 pages.

Wein, Wolfgang, "Intensity Based Rigid 2D-3D Registration Algorithms for Radiation Therapy", Dec. 15, 2003, 100 pages.

G. P. Penney, J. Weese, "A comparison of similarity measures for use in 2D-3D medical image registration," IEEE Trans. Med. Imag., vol. 17, Aug. 1998, pp. 586-595.

R. McLaughlin et al, "A comparison of intensity-based registration and feature-based registration for neurointervention," in Lecture Notes in Computer Science, T. Dohi and R. Kikinis, Eds. Berlin, Germany: Springer-Verlag, 2002, vol. 2489, Proc. MICCAI'02, pp. 517-524.

J. Weese et al, "Fast Voxel-Based 2D/3D Registration Using A Volume Rendering Method Based On Sharp-Warp Factorization" in SPIE Medical Imaging 1999: Image Processing, 1999, pp. 802-810.

* cited by examiner

MULTI-PHASE REGISTRATION OF 2-D X-RAY IMAGES TO 3-D VOLUME STUDIES

CROSS-REFERENCE TO RELATED APPLICATIONS

This application is related to U.S. patent application Ser. No. 10/652,786, titled "Apparatus and Method for Registering 2D Radiographic Images With Images Reconstructed From 3D Scan Data," filed Aug. 29, 2003. This application is also related to U.S. patent application Ser. No. 10/652,717, titled "Apparatus and Method for Determining Measure of Similarity Between Images," filed Aug. 29, 2003.

TECHNICAL FIELD

Embodiments of the invention relate to the field of medical imaging and, in particular, to the registration of medical images.

BACKGROUND

Radiosurgery and radiotherapy systems are radiation treatment systems that use external radiation beams to treat pathological anatomies (e.g., tumors, lesions, vascular malformations, nerve disorders, etc.) by delivering a prescribed dose of radiation (e.g., X-rays or gamma rays) to the pathological anatomy while minimizing radiation exposure to surrounding tissue and critical anatomical structures (e.g., the spinal chord). Both radiosurgery and radiotherapy are designed to necrotize the pathological anatomy while sparing healthy tissue and the critical structures. Radiotherapy is characterized by a low radiation dose per treatment, and many treatments (e.g., 30 to 45 days of treatment). Radiosurgery is characterized by a relatively high radiation dose in one, or at most a few, treatments.

In both radiotherapy and radiosurgery, the radiation dose is delivered to the site of the pathological anatomy from multiple angles. As the angle of each radiation beam is different, each beam can intersect a target region occupied by the pathological anatomy, while passing through different regions of healthy tissue on its way to and from the target region. As a result, the cumulative radiation dose in the target region is high and the average radiation dose to healthy tissue and critical structures is low. Radiotherapy and radiosurgery treatment systems can be classified as frame-based or image-guided.

In frame-based radiosurgery and radiotherapy, a rigid and invasive frame is fixed to the patient to immobilize the patient throughout a diagnostic imaging and treatment planning phase, and a subsequent treatment delivery phase. The frame is fixed on the patient during the entire process. Image-guided radiosurgery and radiotherapy (IGR) eliminate the need for invasive frame fixation by tracking and correcting for patient movement during treatment.

In image-guided systems, patient tracking during treatment is accomplished by registering 2-dimensional (2-D) in-treatment X-ray images of the patient (indicating where the patient is) to 2-D reference projections of one or more pre-treatment 3-dimensional (3-D) volume studies of the patient (indicating where the patient should be to match the treatment plan), and changing the position of the patient or the radiation source to correct for differences between the two sets of images. The pre-treatment 3-D volume studies may be computed tomography (CT) scans, magnetic resonance imaging (MRI) scans, positron emission tomography (PET) scans or the like.

The reference projections (reference images), known as digitally reconstructed radiographs (DRRs) are generated using ray-tracing algorithms that replicates the known geometry of the in-treatment X-ray imaging system to produce images that have the same scale as the in-treatment X-ray images. Typically, the in-treatment X-ray system is stereoscopic, producing images of the patient from two (or more) different points of view (e.g., orthogonal views), so the images can be used to determine the precise 3-D coordinates of any point in the field of view of the X-ray imaging system.

Types of image-guided radiotherapy and radiosurgery systems include gantry-based systems and robotic-based systems. In gantry-based systems, the radiation source is attached to a gantry that moves around a center of rotation (isocenter) in a single plane. Each time a radiation beam is delivered during treatment, the axis of the beam passes through the isocenter. In some gantry-based systems, known as intensity modulated radiation therapy (IMRT) systems, the cross-section of the beam is shaped to conform the beam to the pathological anatomy under treatment. In robotic-based systems, the radiation source is not constrained to a single plane of rotation.

In image-guided radiosurgery and radiotherapy systems, the registration of the 2-D in-treatment images with the 2-D reference images provides difference information that can be used to change the position of the patient or the radiation source so the actual treatment conforms to the treatment plan. Typically, a set of 2-D in-treatment X-ray images must be registered with a set of 2-D reference images before the application of each radiation treatment beam. A complete treatment may require the application of 100 to 300 separate beams, so the registration process should be both fast and accurate to decrease the total time required for treatment. Unfortunately, conventional registration systems and methods that are accurate are computationally slow, and conventional registration systems that are computationally fast have limited accuracy.

BRIEF DESCRIPTION OF THE DRAWINGS

The present invention is illustrated by way of example, and not by limitation, in the figures of the accompanying drawings in which.

DETAILED DESCRIPTION

In the following description, numerous specific details are set forth such as examples of specific components, devices, methods, etc., in order to provide a thorough understanding of embodiments of the present invention. It will be apparent, however, to one skilled in the art that these specific details need not be employed to practice embodiments of the present invention. In other instances, well-known materials or methods have not been described in detail in order to avoid unnecessarily obscuring embodiments of the present invention. The term "coupled" as used herein, may mean directly coupled or indirectly coupled through one or more intervening components or systems. The term "X-Ray image" as used herein may mean a visible X-ray image (e.g., displayed on a video screen) or a digital representation of an X-ray image (e.g., a file corresponding to the pixel output of an X-ray detector). The term "in-treatment image" as used herein may refer to images captured at any point in time during a treatment delivery phase of a radiosurgery or radiotherapy procedure, which may include times when the radiation source is either on or off. The term IGR as used herein may refer to image-guided radiotherapy, image-guided radiosurgery or both.

Unless stated otherwise as apparent from the following discussion, it will be appreciated that terms such as "processing," "computing," "determining," "estimating," "searching" or the like may refer to the actions and processes of a computer system, or similar electronic computing device, that manipulates and transforms data represented as physical (e.g., electronic) quantities within the computer system's registers and memories into other data similarly represented as physical within the computer system memories or registers or other such information storage, transmission or display devices. Embodiments of the method described herein may be implemented using computer software. If written in a programming language conforming to a recognized standard, sequences of instructions designed to implement the methods can be compiled for execution on a variety of hardware platforms and for interface to a variety of operating systems. In addition, embodiments of the present invention are not described with reference to any particular programming language. It will be appreciated that a variety of programming languages may be used to implement embodiments of the present invention.

Figure 1A:
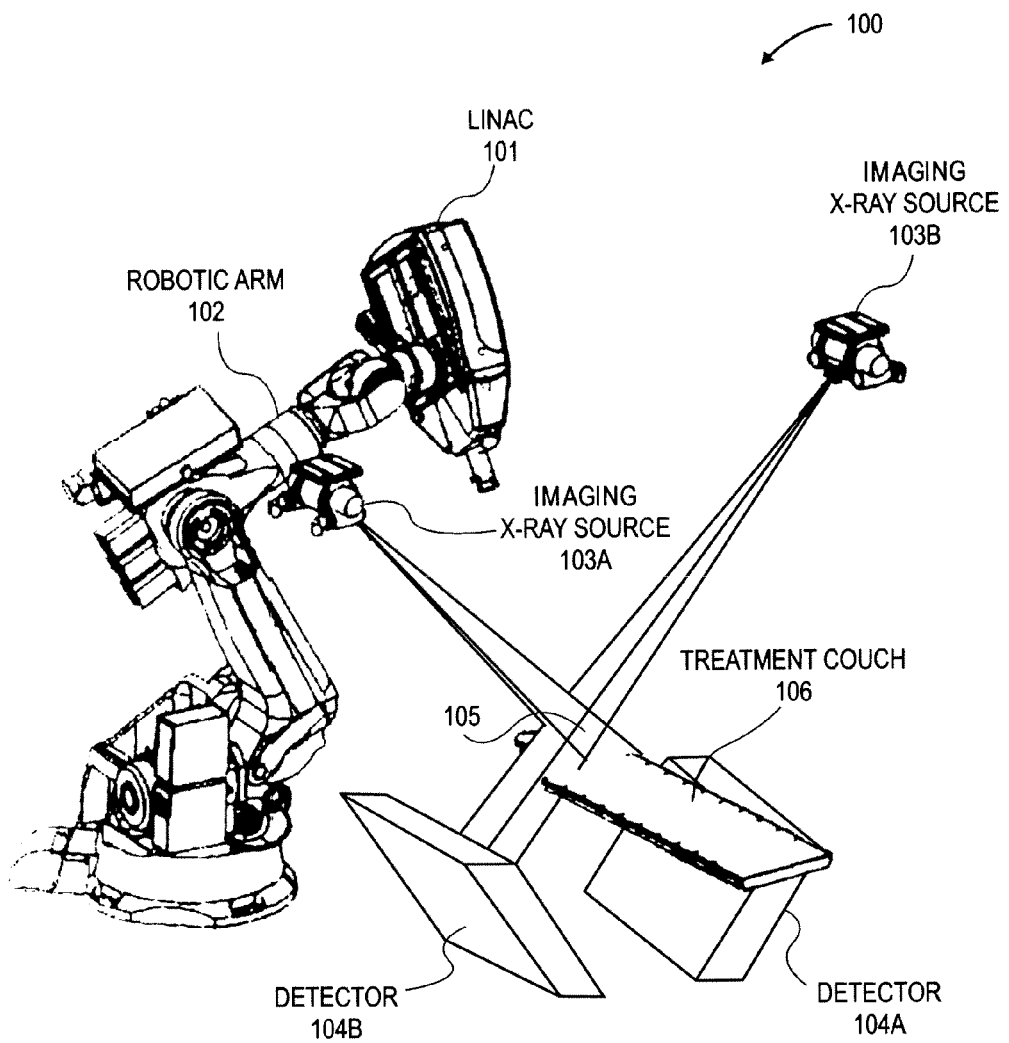
FIG. 1A illustrates an image-guided robotic radiosurgery system in one embodiment.
Figure 1B:
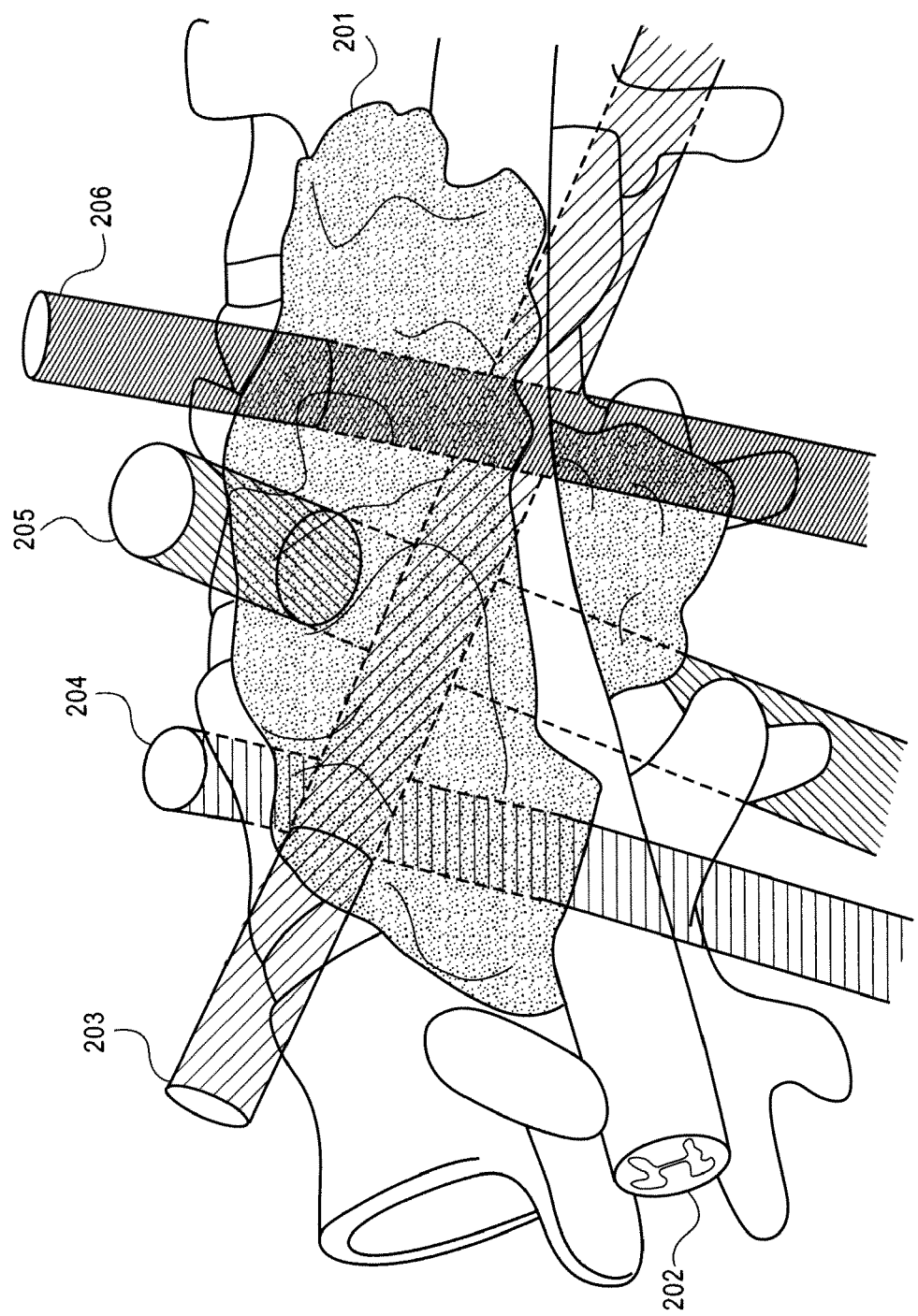
FIG. 1B illustrates non-isocentric radiation treatment in an image-guided radiosurgery system in one embodiment.

FIG. 1A illustrates the configuration of an image-guided, robotic-based radiation treatment system 100, such as the CyberKnife® Radiosurgery System manufactured by Accuray, Inc. of California. In FIG. 1A, the radiation treatment source is a linear accelerator (LINAC) 101 mounted on the end of a robotic arm 102 having multiple (e.g., 5 or more) degrees of freedom in order to position the LINAC 101 to irradiate a pathological anatomy (target region or volume) with beams delivered from many angles, in many planes, in an operating volume around the patient. Treatment may involve beam paths with a single isocenter, multiple isocenters, or with a non-isocentric approach. FIG. 1B illustrates non-isocentric radiation treatment in one embodiment. In FIG. 1B, a pathological anatomy (e.g., a tumor) 201 growing around a spinal cord (202) is treated for example, by radiation treatment beams 203, 204, 205 and 206, which each intersect the pathological target volume without converging on a single point, or isocenter, within the target).

In FIG. 1A, the imaging system may include X-ray sources 103A and 103B and X-ray detectors (imagers) 104A and 104B. The two x-ray sources 103A and 103B may be mounted in fixed positions on the ceiling of an operating room and may be aligned to project imaging x-ray beams from two different angular positions (e.g., separated by 90 degrees) to intersect at a machine isocenter 105 (which provides a reference point for positioning the patient on a treatment couch 106 during treatment) and to illuminate imaging planes of respective detectors 104A and 104B after passing through the patient. In other embodiments, system 100 may include more or less than two X-ray sources and more or less than two detectors, and any of the detectors may be movable rather than fixed. In yet other embodiments, the positions of the x-ray sources and the detectors may be interchanged.

The detectors 104A and 104B may be fabricated from a scintillating material that converts the X-rays to visible light (e.g., amorphous silicon), and an array of CMOS (complementary metal oxide silicon) or CCD (charge-coupled device) imaging cells that convert the light to a digital image that can be compared with the reference images during the registration process.

Figure 2A:
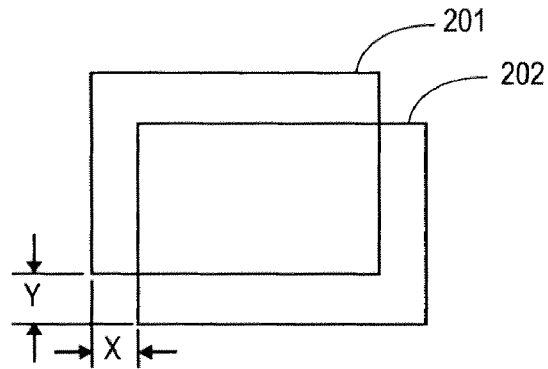
FIGS. 2A-2D illustrate examples of image misregistration.
Figure 2B:
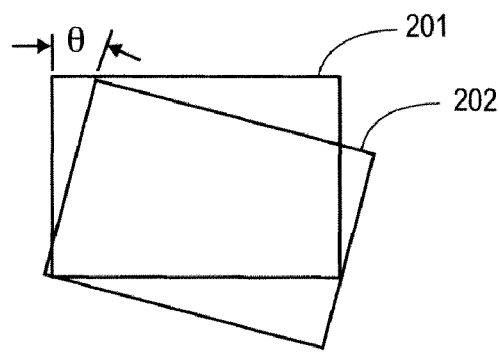
Figure 2C:
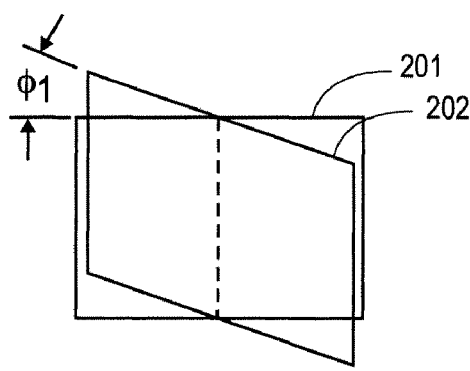
Figure 2D:
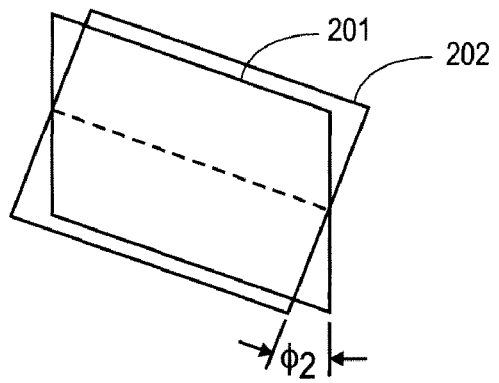

FIGS. 2A through 2D illustrate the ways in which two 2-D images 201 and 202 may be misaligned. FIG. 2A illustrates in-plane translation, which can be described in terms of linear displacement in two dimensions, x and y, between images 201 and 202. FIG. 2B illustrates in-plane rotation, which can be described in terms of a rotation, θ between image 201 and image 202. Together, FIGS. 2A and 2B define the dimensional space of in-plane transformations, which include x, y and θ. FIG. 2C illustrates a first type of out-of-plane rotation, which can be described in terms of an angular rotation, φ1, of image 202 with respect to one axis (e.g., a vertical axis) of image 201. FIG. 2D illustrates a second type of out-of-plane rotation, which can be described in terms of an angular rotation, φ2, of image 202 with respect to another axis (e.g., a horizontal axis) of image 201.

In the following descriptions of embodiments of the invention, CT scans may be used as an exemplary imaging modality for 3-D volume studies. Similarly, X-ray imaging may be used as an exemplary imaging modality for 2-D in-treatment imaging. Those skilled in the art will understand that other 3-D imaging modalities (e.g., MRI, PET, 3-D ultrasound) and other 2-D imaging modalities (e.g., fluoroscopy) may be used to equal effect in other embodiments.

Methods and apparatus are described for tracking patient movement during image-guided radiotherapy and/or radiosurgery by using multi-phase registration of 2-D in-treatment X-ray images to pre-treatment 3-D volume studies. In one embodiment, digitally reconstructed radiographs (DRR's) are generated offline from a 3-D volume study before treatment, and are used as reference images to register a patient's position. Stereoscopic X-ray images (e.g., two or more 2-D projections of the patient volume from different points of view) of the patient are acquired during treatment, and multi-phase registration is used to register the DRRs with the X-ray images in two or more projections. The registration in each projection is carried out independently, and the results are combined and converted to a 3-D rigid transformation. In-plane transformations and out-of-plane rotations between the DRR's and the X-ray images are estimated using different search methods and similarity measures in each phase of the registration process to achieve registration accuracy and computational speed.

In general, methods used in 2-D to 3-D registration can be organized into two classes. The first class is based on image features (see, e.g., U.S. Pat. No. 5,901,199 by Murphy et al.). Image features may be anatomical edges, image gradients, contours, object surfaces, segmented objects or similar anatomical features. The accuracy of the registration may depend on the accuracy of feature extraction such as edge detection and object segmentation, for example. The principal advantage of feature extraction methods is fast computation. However, feature extraction does not use all of the available of image data, and the accuracy of the registration may be compromised.

The second class of registration method is based on image intensity (see, e.g., G. P. Penney, J. Weese, "A comparison of similarity measures for use in 2D-3D medical image registration," *IEEE Trans. Med. Imag.*, vol. 17, pp. 586-595, August, 1998), where the full content of an image is used for registration to yield improved accuracy. The improved accuracy comes at the cost of greater computational intensity (more data), but the image intensity methods are more easily automated because they do not rely on artificial intelligence measures that are required for feature extraction (see, e.g., R. McLaughlin et al, "A comparison of intensity-based registration and feature-based registration for neurointervention," in *Lecture Notes in Computer Science*, T. Dohi and R. Kikinis, Eds. Berlin, Germany: Springer-Verlag, 2002, vol. 2489, Proc. MICCAI'02, pp. 517-524)

Image-guided radiosurgery systems (such as the CyberKnife® Radiosurgery System manufactured by Accuray, Inc. of California) require an automatic, accurate, fast and robust (e.g., tolerant of large initial errors) tracking method for frequent patient alignment and patient position correction. In order to meet these requirements, and to make the tracking algorithm useful in practice, certain issues may need to be addressed.

First, the imaging modalities used for the pre-operative 3-D volume study and the in-treatment 2-D imaging may differ with respect to spatial resolution and image quality. For example, the resolution and quality of the in-treatment X-ray images may be superior to that of DRR images. Therefore, the DRR images should be generated such that their appearance closely matches the X-ray images for better registration Second, the energy used in the generation of the in-treatment X-ray images may be different from that used in the pre-operative scan (e.g., CT scan). The scan energy cannot be changed post-scan. However, the energies during X-ray image acquisition can be adjusted. The overall characteristics of X-ray images change with the X-ray energies. Accordingly, the registration results will vary as the X-ray energy is varied. Therefore, for reliable and robust patient alignment, the tracking results should be insensitive to moderate variations in X-ray energies.

Third, out-of-plane rotations are more difficult to estimate than in-plane translations and rotations, because the image variations in a 2-D plane due to out-of-plane rotations are subtle (e.g., small changes in out-of-plane rotations correspond to very small changes in the 2-D in-treatment X-ray images). Detection of these subtle changes requires a robust similarity measure for accurate image registration.

Fourth, during initial patient alignment, the initial misregistration may be large. Providing an initial guess, which is close to the correct transformation, helps the registration to converge to a global optimum but requires some user interactions. Therefore, automatic and fast detection of large displacements requires a robust search method.

In one embodiment, two orthogonal projections are utilized. In each projection, a set of DRR images corresponding to different out-of-plane rotations are pre-generated off-line and used as reference images. The in-plane transformations and out-of-plane rotations in both projections are estimated independently via registration of the X-ray image to the DRR image set, and then combined and converted to a 3-D rigid transformation. Estimations of transformation parameters between the in-treatment 2-D projections of the patient volume and the 2-D reference images of the patient volume are performed in multiple phases. In each phase, different combinations of search methods and similarity measures may be used to determine the transformation parameters.

In one embodiment, patient tracking during an IGR procedure may be accomplished by means of registration of 2-D X-ray images to a 3-D CT volume, using. DRR images generated from the 3-D CT volume. On-line DRR generation from the CT volume may be too slow for fast registration, because a reasonably accurate registration entails a large number of DRR images (e.g., 30 or more). For a large number of DRR images, even fast volume rendering techniques (see, e.g., J. Weese et al, "Fast Voxel-Based 2D/3D Registration Using A Volume Rendering Method Based On Sharp-Warp Factorization" in *SPIE Medical Imaging* 1999: *Image Processing*, 1999, pp. 802-810) are not fast enough to achieve a fast registration. Off-line DRR generation can be performed to mitigate this problem. In one embodiment, a set of DRRs with pre-defined out-of-plane rotations (e.g., in one degree increments corresponding to an expected range of patient movement) may be generated off-line prior to registration and used as the reference images to estimate out-of-plane rotations during registration. As described below, the number of DRRs required for registration may be reduced by making simplifying approximations of the geometric relationship between the position of the patient (a 3-D object) and the 2-D image projections produced by the in-treatment X-ray imaging system.

Figure 3:
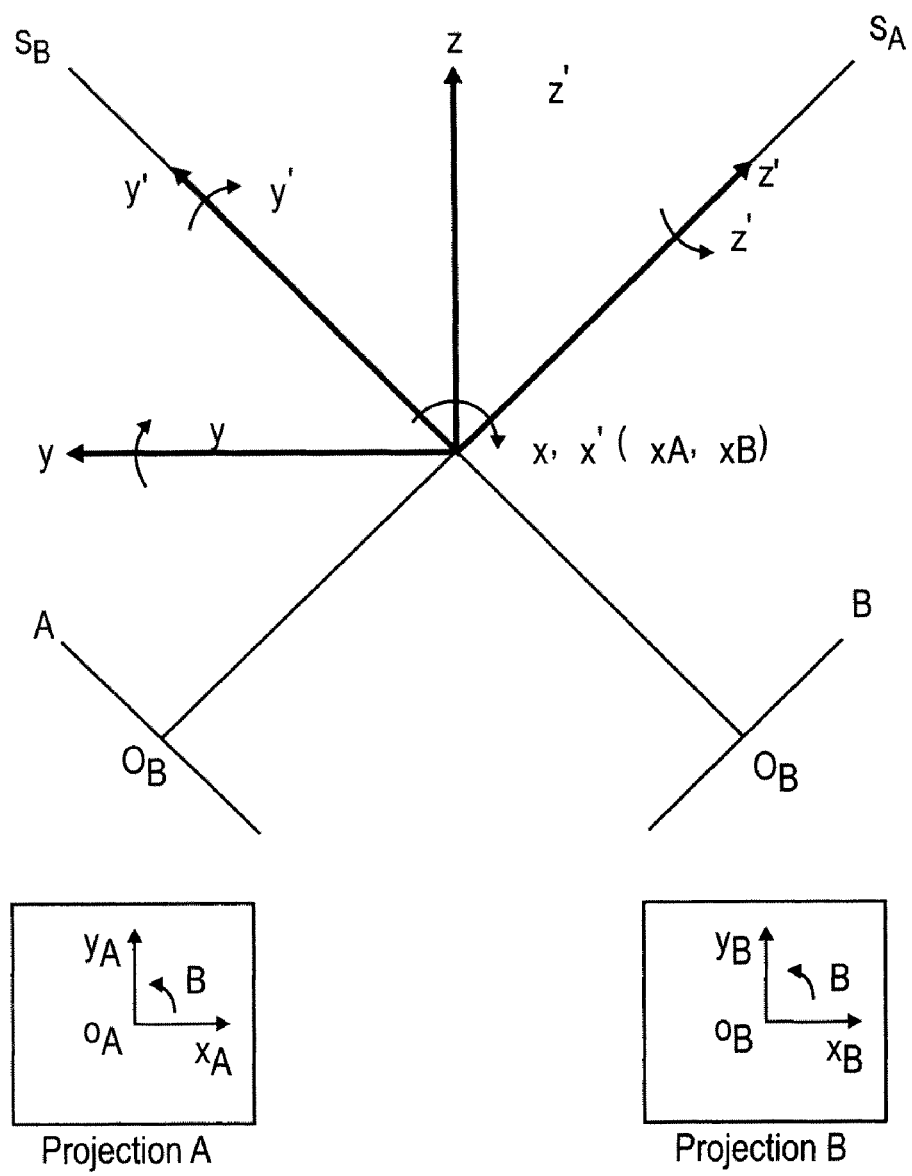
FIG. 3 illustrates a reference coordinate system in one embodiment.

For certain anatomical structures (e.g., the skull), a 3-D rigid transformation may be assumed for modeling patient movement. The 3-D rigid transformation may be described using six degrees of freedom: three translations and three rotations (roll, pitch and yaw) about the three axes. Two orthogonal (or other pair of non-coaxial) X-ray projections may be used to solve these six parameters. FIG. 3 illustrates geometric relationships between a 3-D object (e.g., the patient) and the two 2-D X-ray projections in two X-ray detectors A and B, respectively. X-ray detectors A and B may obtain their X-ray projections from their respective X-ray sources, $s_A$ and $s_B$, which pass X-rays through the patient.

A 3-D coordinate system (xyz) may be defined for the patient, where the x-axis points inward into the page (not indicated in FIG. 3). The patient position is represented by three translations and three rotations $(x,y,z,\theta_x,\theta_y,\theta_z)$. The 2-D projections, Projection A and Projection B, are viewed from the directions $o_A s_A$ and $o_B s_B$, respectively. The direction of axis $x_A$ in the coordinates of projection A is opposite to that of axis x in the 3-D patient coordinates. The direction of axis $x_B$ in the coordinates of projection B is the same as that of axis x in the 3-D patient coordinates. In order to establish the relationship between the 3-D coordinate system and the two projection coordinate systems, another 3-D coordinate system (x'y'z') may be introduced, as shown in FIG. 3, where the 3-D rigid transformation is described by $(x',y',z',\theta_{x'},\theta_{y'},\theta_{z'})$. The relationships of the 3-D rigid transformation between the two coordinate systems may be expressed as $$x = x', \; y = (y' - z')/\sqrt{2}, \; z = (y' + z')/\sqrt{2}, \quad (1)$$
$$\theta_x = \theta_{x'}, \; \theta_y = (\theta_{y'} - \theta_{z'})/\sqrt{2}, \; \theta_z = (\theta_{y'} + \theta_{z'})/\sqrt{2}.$$

In the 2-D coordinate system $(x_A y_A)$ for projection A, the 3-D rigid transformation is decomposed into the in-plane transformation $(x_A, y_A, \theta_A)$ and two out-of-plane rotations $(\theta_{x_A}, \theta_{y'})$. Similarly, in the 2-D coordinate system $(x_B y_B)$ for projection B, the decomposition consists of the in-plane transformation $(x_B, y_B, \theta_B)$ and two out-of-plane rotations $(\theta_{x_B}, \theta_{z'})$. The 3-D rigid transformation of equation (1) may be simplified by noting that the use of two projections overconstrains the solution to the six parameters of the 3-D patient coordinate system. The translation $x_A$ in projection A is the same parameter as $x_B$ in projection B, and the out-of-plane rotation $\theta_{x_A}$ in projection A is the same as $\theta_{x_B}$ in projection B. If $\alpha_A$ and $\alpha_B$ are the geometric amplification factors (e.g., scale factors related to source-to-patient and patient-to-detector distances) for projections A and B, respectively, then the translations between the coordinate system (x'y'z') and the 2-D coordinate systems have the following relationships:

$$x' = (\alpha_B x_B - \alpha_A x_A)/2, \ y' = \alpha_A y_A, \ z' = \alpha_B y_B. \quad (2)$$

For projection A, given a set of reference DRR images which correspond to different combinations of the two out-of-plane rotations $(\theta_{x_A}, \theta_{y'})$, the 2-D in-plane transformation $(x_A, y_A, \theta_A)$ may be estimated by a 2-D to 2-D image comparison, and the two out-of-plane rotations $(\theta_{x_A}, \theta_{y'})$ may be calculated by best matching the X-ray image to the set of DRR references as described below, using similarity measures. Likewise, the same process may be used to solve the 2-D in-plane transformation $(x_B, y_B, \theta_B)$ and the out-of-plane rotations $(\theta_{x_B}, \theta_{z'})$ for the projection B. As described below, the in-plane transformation and out-of-plane rotations may be obtained by registration between the X-ray image and the set of DRR images, independently for both projection A and projection B. When a reference DRR image with a matching out-of-plane rotation is identified, the in-plane rotation and the out-of-plane rotation have the following relations:

$$\theta_{y'} = \theta_B, \ \theta_{z'} = \theta_A. \quad (3)$$

If the out-of-plane rotation $\theta_{y'}$ is ignored in the set of reference DRR images for projection A, the in-plane transformation can be approximately described by $(x_A, y_A, \theta_A)$ when $\theta_{y'}$ is small (e.g., less than 5°). Once this simplifying assumption is made, and given the set of reference DRR images which correspond to various out-of-plane rotations $\theta_{x_A}$, the in-plane transformation $(x_A, y_A, \theta_A)$ and the out-of-plane rotation $\theta_{x_A}$ may be solved by one or more multi-phase registration methods described in detail below. A corresponding simplification may be made for projection B. In one embodiment, the range of out-of-plane rotations defined for the reference DRR images may be limited to approximately ±5° because out-of-plane rotations may be expected to be small after an initial patient alignment.

Given the results $(x_A, y_A, \theta_A, \theta_{x_A})$ in projection A and $(x_B, y_B, \theta_B, \theta_{x_B})$ in projection B, the approximation of the 3-D rigid transformation in the patient coordinate system may be obtained using the following expressions $$x = (-\alpha_A x_A + \alpha_B x_B)/2, \quad (4)$$
$$y = (\alpha_A y_A - \alpha_B y_B)/\sqrt{2},$$
$$z = (\alpha_A y_A + \alpha_B y_B)/\sqrt{2},$$
$$\theta_x = (\theta_{x_A} + \theta_{x_B})/2,$$
$$\theta_y = (\theta_B - \theta_A)/\sqrt{2},$$
$$\theta_z = (\theta_B + \theta_A)/\sqrt{2}.$$

Figure 4:
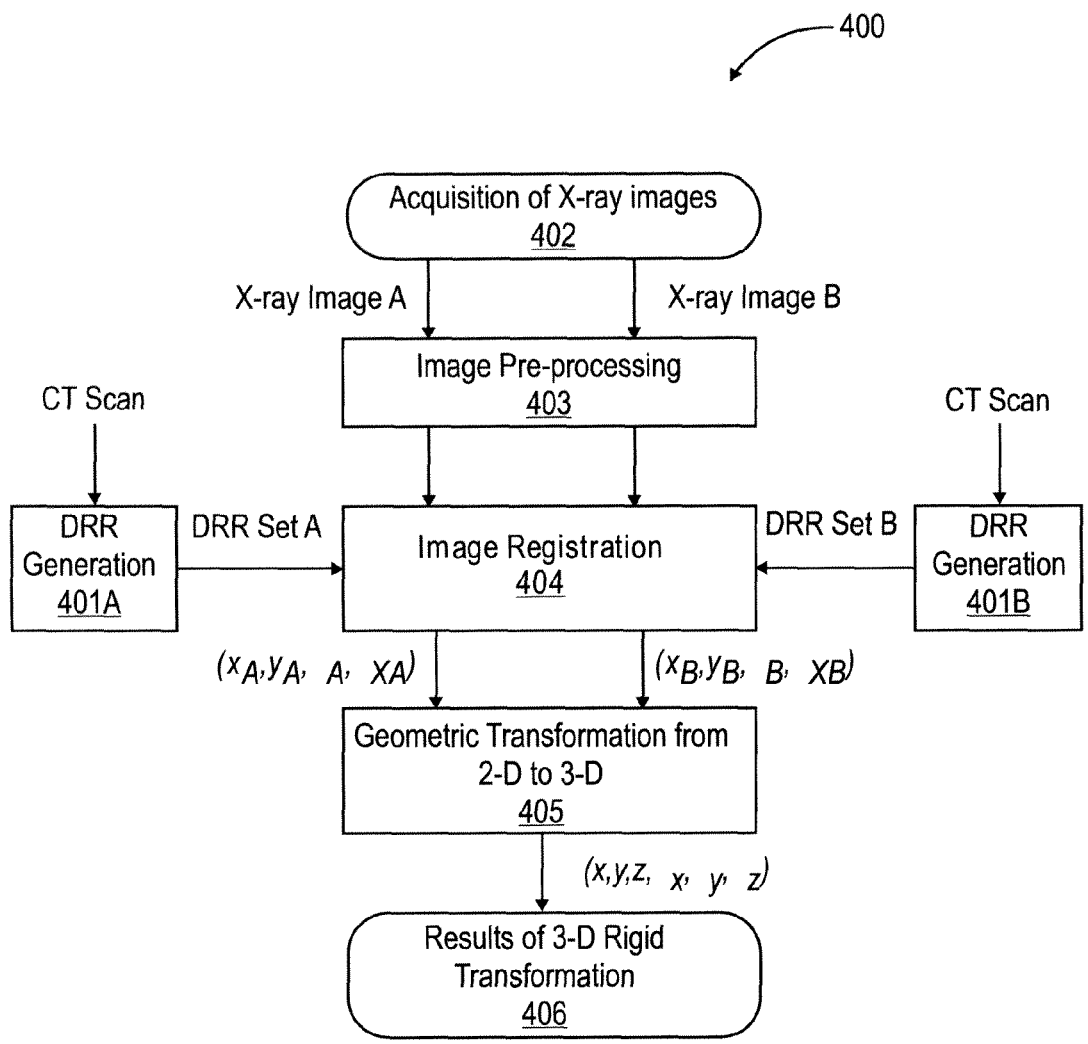
FIG. 4 is a flowchart illustrating patient tracking in one embodiment.

FIG. 4 is a flowchart illustrating a method 400 for patient tracking in one embodiment. At step 401a, a set of reference DRR images is generated off-line for projection A. At step 401b, a set of reference DRR images is generated off-line for projection B. This process may be carried out after radiation treatment planning and before radiation treatment delivery. In the course of patient alignment and treatment, the real time X-ray projection images may be acquired (step 402) and pre-processed (step 403). In one embodiment, preprocessing may include matching scale, bit-depth, intensity or other image parameters as are known in the art. At step 404, the processed X-ray image in each projection is independently registered against the reference DRR images, utilizing the multi-phase registration methods described below. The results of registration $(x_A, y_A, \theta_A, \theta_{x_A})$ in projection A and $(x_B, y_B, \theta_B, \theta_{x_B})$ in projection B are then combined in a 2-D to 3-D geometric transformation (step 405) to produce the final six rigid transformation parameters $(x, y, z, \theta_x, \theta_y, \theta_z)$. At step 406, the 3-D rigid transformation is applied to correct the patient position and/or the position of the radiation source (e.g., LINAC 101)

The registration method may be implemented in a multi-phase framework. The in-plane transformations and the out-of-plane rotations for each of projections A and B may be estimated separately and iteratively at different phases. At least two different similarity measures and three different search methods may be applied at different registration phases to minimize the required computation time and maximize the accuracy of the registration. In the following, a design of a generic registration algorithm is first described, and then the various similarity measures and the search methods are described in detail.

As described above, the out-of-plane rotations may be estimated from reference DRR images of predefined out-of-plane rotations, and the in-plane transformation parameters $(x, y, \theta)$ may be computed directly from the 2-D in-treatment X-ray images. The registration method relies on the following observations: (1) detection of out-of-plane rotations is comparatively more difficult than detection of in-plane transformations. Hence, a more robust similarity measure should be used for out-of-plane rotations, compared to in-plane transformations, for adequate accuracy; (2) The in-plane transformations may safely converge to an approximate solution by using a nominal reference (e.g., zero degree) DRR image, even when large out-of-plane rotations are present in the 3-D rigid transformation. It is also observed that the out-of-plane rotations may be detected with reasonably good accuracy using an in-plane transformation as an initial guess, which has already been roughly estimated using the simplifying approximations described above; (3) a non-complex similarity measure may be used during an initial search of the in-plane transformation, so that an approximate estimation may be achieved in a short period of time.

Figure 5:
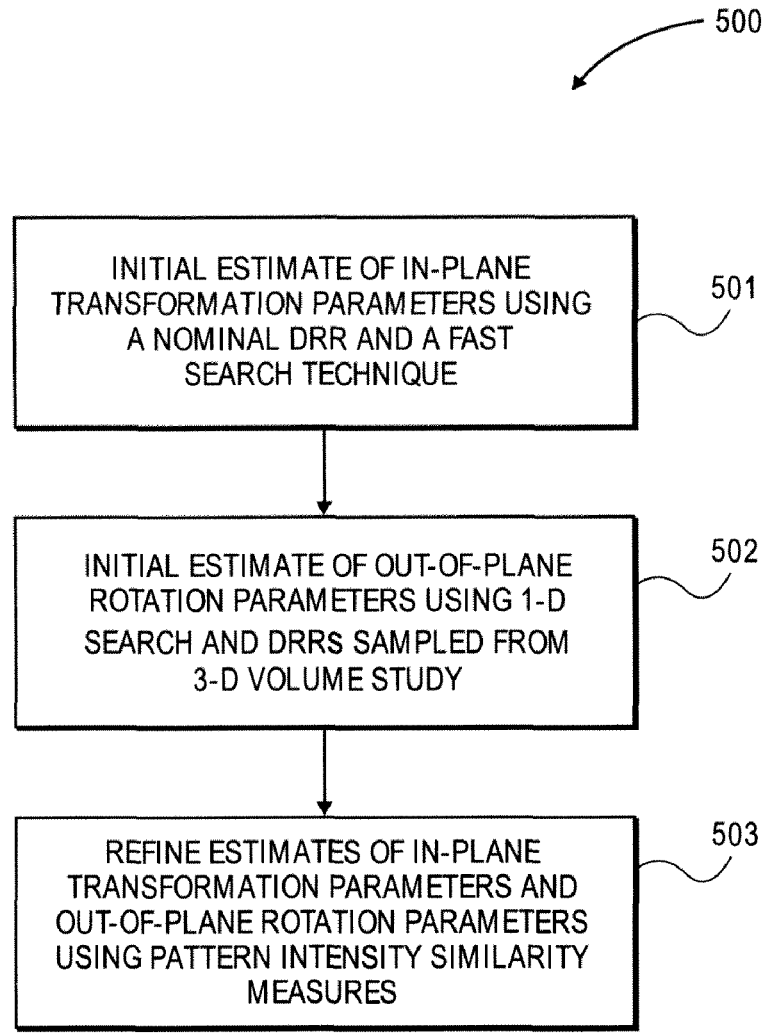
FIG. 5 is a flowchart illustrating a generic method of image registration in one embodiment.

Based on the foregoing observations, the registration algorithm may be implemented in a multi-phase framework. A flowchart of a generic three-phase image registration method 500 is illustrated in FIG. 5. In a first phase (step 501), the in-plane transformation parameters $(x, y, \theta)$ may be initially estimated using the nominal (e.g., zero degree out-of-plane rotation) DRR image. The three parameters may be quickly searched via multi-resolution matching, using SSD as the similarity measure. In this phase, the desired pixel accuracy for the translations and half-degree accuracy for the in-plane rotation may be achieved, without the need for expensive and slow floating-point computation.

In a second phase (step 502), the out-of-plane rotation may be separately searched in one dimension, based on the approximate results of $(x, y, \theta)$ obtained in the first phase. As described below, an optimized pattern intensity may be used as a similarity measure to determine the reference DRR image corresponding to an out-of-plane rotation. The search space during this phase may be the full search range of out-of-plane rotation angles, sampled at one-degree intervals for the initial estimation, for example.

In a third phase (step 503), the in-plane transformation and the out-of-plane rotation may be refined iteratively, using a pattern intensity similarity measure for increased accuracy. There may be two steps in the iteration. In the first step, the previously estimated in-plane transformation is refined via a steep descent minimization and, in the second step; the out-of-plane rotation is refined using a one-dimensional (1-D) search. These two steps may be repeated for a specified number of iterations or until a specified accuracy is obtained. The final registration results are the in-plane transformation and the out-of-plane rotation parameters. The use of different similarity measures in different phases of the registration process may improve the overall speed and accuracy of the final registration Similarity measures compare an X-ray image with a set DRR images to find the in-plane transformation parmeters and the out-of-plane rotation parameters required to register the X-ray image. Standardized pattern intensity difference and gradient difference similarity measures are similarity measures, known in the art, which are robust similarity measures. However, such methods may not be computationally efficient. In one embodiment, the present invention utilizes a pattern intensity similarity measure that is more computationally efficient than standard pattern intensity and is more accurate in determining out-of-plane rotations than gradient difference similarity measures.

Figure 6:
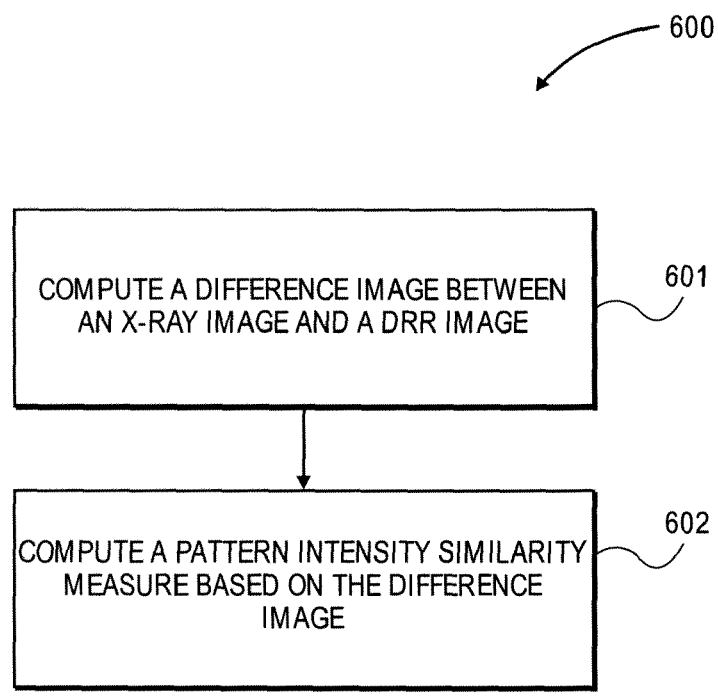
FIG. 6 is a flowchart illustrating a method for constructing a pattern intensity similarity measure in one embodiment.

Pattern intensity and gradient difference have the same mathematical meanings (see, e.g., G. P. Penney, J. Weese, "A comparison of similarity measures for use in 2D-3D medical image registration," *IEEE Trans. Med. Imag.*, vol. 17, pp. 586-595, August, 1998), but gradient difference is much more efficient in terms of computational cost than pattern intensity. Gradient difference formulations contains two terms, representing gradients in two mutually orthogonal directions (e.g., 0 degrees and 90 degrees). Pattern intensity has two additional terms, gradients bisecting the axes of the gradient difference formulation (e.g., 45 degrees and 135 degrees). FIG. 6 illustrates a method 600 for constructing an optimized pattern intensity similarity measure may therefore include the following steps. At step 601, a difference image between an X-ray image and a DRR image may be computed as:

$$I_{dif}(i,j) = I_{Xray}(i,j) - I_{DRR}(i,j). \quad (5)$$

where i and j are 2-D pixel coordinates in the respective X-ray and DRR images. At step 602, a pattern intensity similarity measure is computed. Pattern intensity operates on the difference image and may be expressed as an asymptotic function of the gradients of the difference image:

$$S_{PI} = \sum_{i,j} \sum_{k,l \in R} \frac{\sigma^2}{\sigma^2 + (I_{dif}(i,j) - I_{dif}(i+k, j+l))^2}, \quad (6)$$

where σ is a weighting constant and R is a neighborhood using the pixel (i,j) as the center point.

Equation (6) for pattern intensity has several advantages. First, the difference image acts as a low-pass filter to effectively remove soft tissue while retaining high-frequency components corresponding to skeletal structures. This characteristic makes the algorithm robust to some amount of brightness intensity differential between X-ray and DRR images. Second, due to the asymptotic nature of the function, the measure is less sensitive to outlier pixels contaminated with random noise. Lastly, because the asymptotic function quickly approaches zero when its variable (for instance, $(I_{dif}(i,j) - I_{dif}(i+k, j+l))$ in equation (6)) increases, large intensity differences such as image artifacts have the same effects on the similarity measure function regardless of their magnitude. As a result, pattern intensity is less sensitive to image artifacts.

The sensitivity of the solution to variations of X-ray image may be minimized by careful selection of weighting constant σ. The stability of the results against X-ray image noise improves with an increased value of this constant. However, this choice is a tradeoff between stability and accuracy. When σ is too large, small image details may be obscured. In one embodiment, the value of σ may be selected to be in the range of 4 to 16.

The neighborhood R may be defined such that gradients in four directions are considered: horizontal, vertical, 45° diagonal and 135° diagonal. Based on this neighborhood, the pattern intensity may be expressed as $$S_{OPI} = \sum_{i,j} \frac{\sigma^2}{\sigma^2 + (I_{dif}(i,j) - I_{dif}(i, j-1))^2} + \\ \sum_{i,j} \frac{\sigma^2}{\sigma^2 + (I_{dif}(i,j) - I_{dif}(i-1, j))^2} + \\ \sum_{i,j} \frac{\sigma^2}{\sigma^2 + (I_{dif}(i,j) - I_{dif}(i-1, j-1))^2} + \\ \sum_{i,j} \frac{\sigma^2}{\sigma^2 + (I_{dif}(i,j) - I_{dif}(i-1, j+1))^2}. \quad (7)$$

Because the pattern intensity in equation (7) has two more terms than gradient difference, it includes more image information resulting in a more accurate registration for out-of-plane rotations.

The similarity measure in equation (7) is computationally intensive. To achieve a fast registration, a simple and efficient similarity measure should be used in the initial search stage. The sum of squared differences (SSD), is a simple similarity measure known in the art, and is commonly used in motion estimation for real-time video processing and also in intra-modality medical image registration. Its main advantage is reduced computation cost while retaining reasonably good accuracy. A disadvantage is that the solution is sensitive to image noise, artifacts and intensity difference between the X-ray and DRR images. A closely related similarity measure known in the art, the sum of absolute differences (SAD), may also be used with similar advantages and disadvantages. As a result, SSD or SAD may be used in the first and/or second phase of the registration method to obtain approximate results. The optimized pattern intensity described above may then be used to further refine the registration results. In the multi-phase registration method described previously, three search methods may be used at different registration phases to minimize computation time.

Figure 7A:
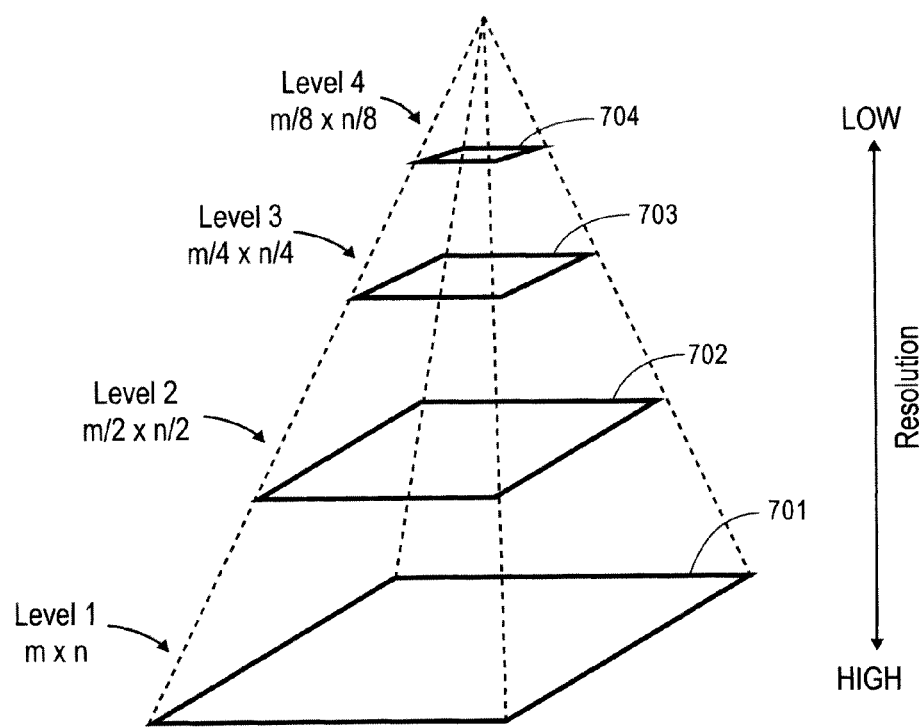
FIG. 7A illustrates multi-resolution matching in one embodiment.

Multi-resolution matching (also known as multi-level matching) is a fast search method for estimating the initial in-plane transformation parameters that will be refined in subsequent search phases. In one embodiment, as illustrated in FIG. 7A, three image resolutions 702 (Level 2), 703 (Level 3) and 704 (Level 4) may be defined with respect to an original X-ray image 701 Level 1), which may be used as the highest resolution image. Successively lower resolution images may be generated by sub-sampling pixels from the original X-ray image 701. In FIG. 7A, resolution Level 1 is represented by the original X-ray image 701, which may contain m×n image pixels. A lower resolution image 702 is formed at Level 2 by selecting every other image pixel (sampling rate of ½) from the Level 1 image such that the Level 2 image contains m/2×n/2 image pixels. The sub-sampling process may be repeated at Level 3 and Level 4 to produce image 703 with m/4×n/4 image pixels and image 704 with m/8×n/8 image pixels. In other embodiments, the number of resolution levels and/or the sampling rate may be different.

The basic idea of multi-resolution matching is to match the images at each level successively, starting with the lowest resolution. The results at the lower resolution serve as rough estimates of the in-plane transformation parameters $(x,y,\theta)$ and reduce the risk of getting trapped in a local optimum of a similarity measure, as described below. The estimates of the in-plane transformation parameters $(x,y,\theta)$ at the lower resolution level are then passed to the next highest resolution level, where the parameters $(x,y,\theta)$ are refined using the higher resolution image. In the final matching results, the accuracy of the in-plane translations depends on the spatial resolution of the highest resolution image (e.g., image 701). The accuracy of the in-plane rotation depends on the sampling intervals of the in-plane rotated DRR reference images.

Multi-resolution matching does not eliminate the risk that the similarity measure used at low resolution levels may converge to a local optimum far away from the global optimum. In such a case, the result of further matching at subsequent higher resolution levels will most likely not converge to the global optimum. To overcome this risk, multiple candidates of estimates may be used. A sorted list of candidates with the best matches from the lower resolution level is passed to the next highest resolution level. The candidates may be ranked by their SSD or SAD values.

Steepest descent minimization search uses the first order derivatives of a similarity measure with respect to the in-plane transformation parameters to determine the directions that converge most rapidly toward the minimum. Steepest descent minimization may be used only during refinement of the in-plane transformation parameters $(x,y,\theta)$. Because approximate results have already been calculated in the initial search phase prior to refinement, as described in the tracking method illustrated in FIG. 4, the search ranges used at this point for the in-plane translations and rotation are of much smaller magnitude. As a result, this phase may need only a few iterations to reach a stable solution.

A 1-D search may be used to determine an out-of-plane rotation because it may be calculated separately. In the initial out-of-plane rotation search, a rough rotation may be determined using the full range of reference DRR images sampled at every one-degree, for example. During refinement, a smaller search range centered at the previously estimated angle may be used to refine the reference. Then the final rotation may be calculated using, for example, a cubic spline interpolation.

Figure 7B:
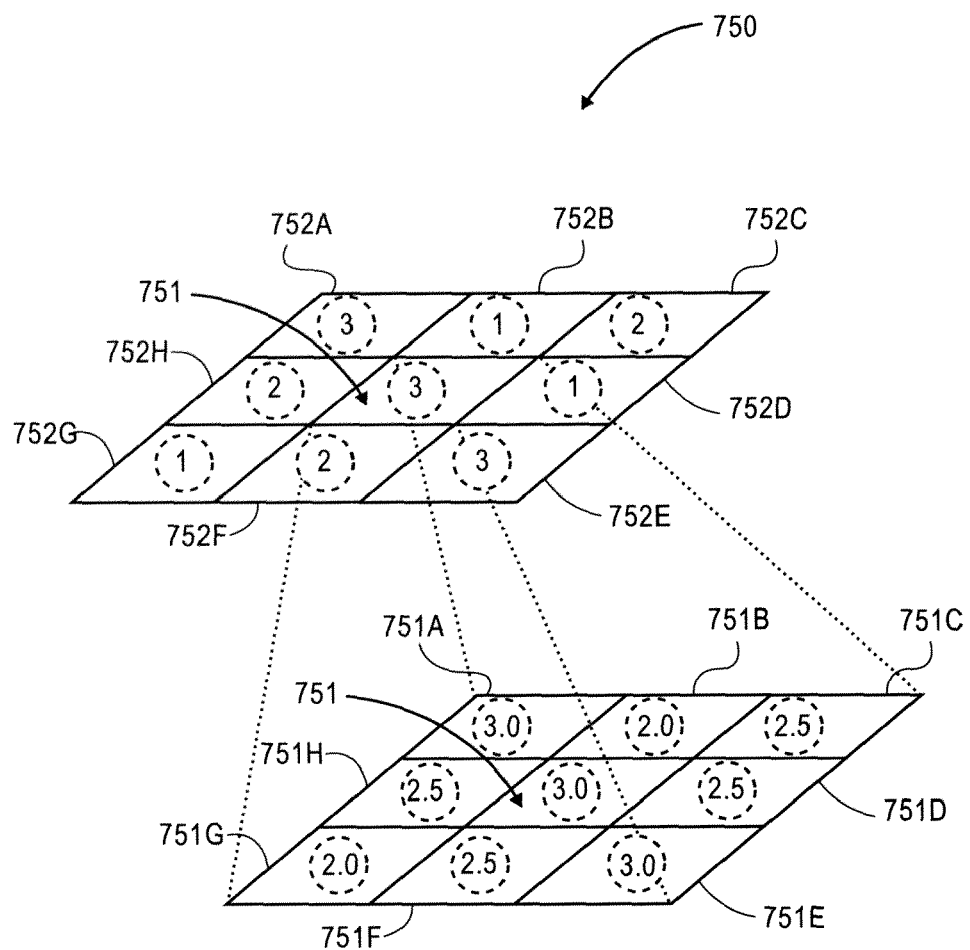
FIG. 7B illustrates 2-D sub-pixel matching in one embodiment.

Sub-pixel matching is a search method that may be used to refine initial search results. An example of sub-pixel matching is illustrated in FIG. 7B. In FIG. 7B, a pixel 751 in a pixel array 750 has eight nearest neighbor pixels 752a through 752h, where each pixel has a pixel value (circled) representing intensity. Pixel 751 may be mapped into an array of sub-pixels 751a through 751i, for example, where the values assigned to the array of sub-pixels are interpolated between the value of pixel 751 and its nearest neighbor pixels 752a through 752h. The process may be repeated to map all the pixels of pixel array 750 into subpixel arrays. An image formed from all the sub-pixel arrays will have an increased sensitivity to small misregistrations.

Figure 8:
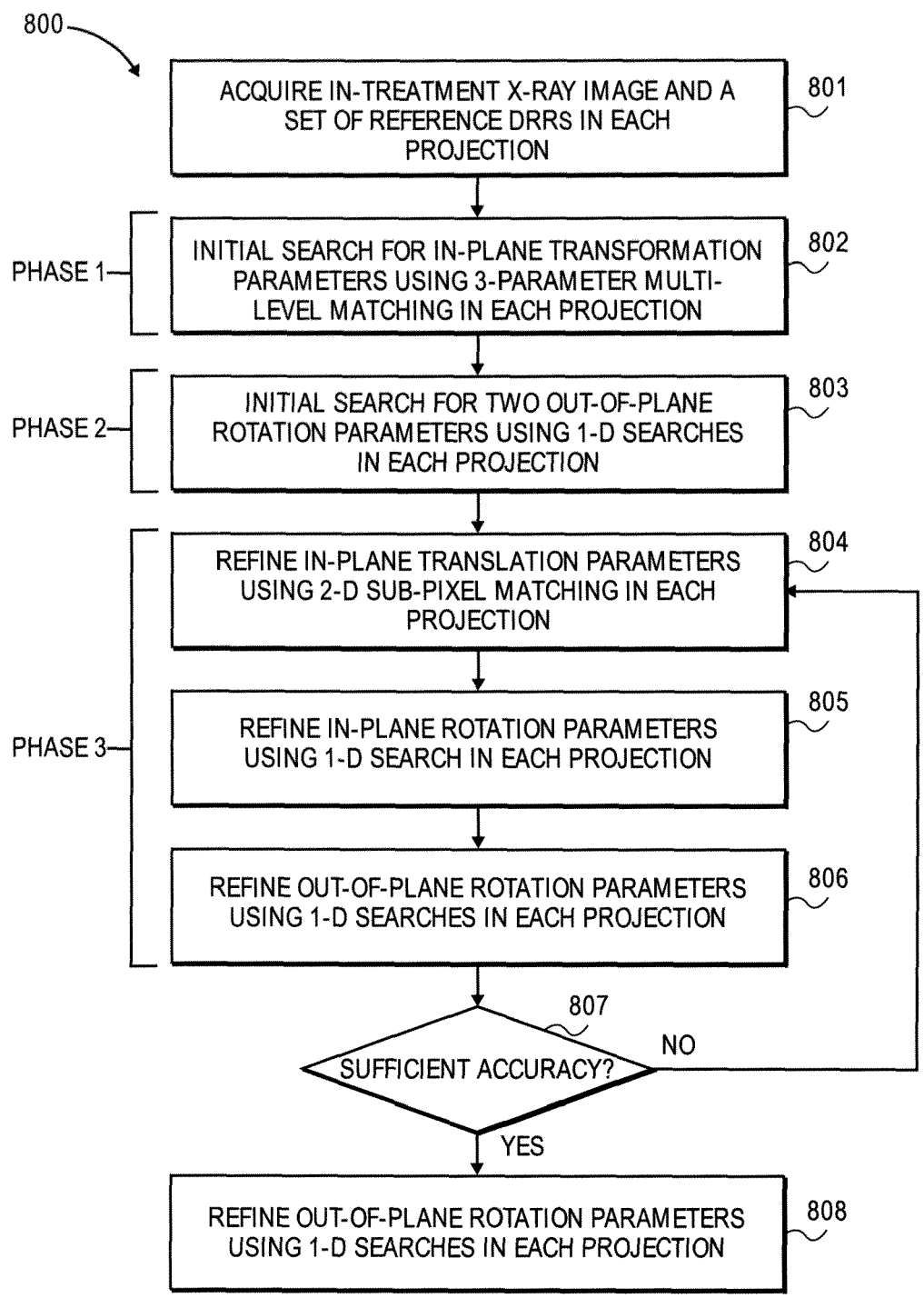
FIG. 8 is a flowchart illustrating a variation of a method of image registration in one embodiment.

The registration methods described above may be utilized in different combinations to tailor registration speed and accuracy to a particular image registration scenario. FIG. 8 is a flowchart illustrating a variation 800 of the method of image registration of FIG. 5. In FIG. 8, the method begins with the acquisition of an in-treatment 2-D X-ray and a set of reference DRRs in each projection (e.g., projection A and projection B) (step 801). Next, a first phase of the registration includes an initial search, in each projection, for in-plane transformation parameters using 3-parameter multi-level matching (step 802). Phase 2 of the registration includes an initial search for two out-of-plane rotation parameters in each projection using 1-D searches for each parameter (step 803). Phase 3 of the registration includes: refinement of the in-plane translation parameters in each projection, using 2-D sub-pixel matching (step 804); refinement of the in-plane rotation parameters in each projection, using 1-D searches (step 805); refinement of the out-of-plane rotation parameters in each projection using 1-D searches (step 806); and checking the accuracy of the in-plane registration result in each projection against a target accuracy (step 807). If, at step 807, the accuracy is insufficient, phase 3 may be repeated. If, at step 806, the accuracy is sufficient, then the out-of-plane rotation parameters may be further refined using a 1-D searches in each projection (step 808).

Figure 9:
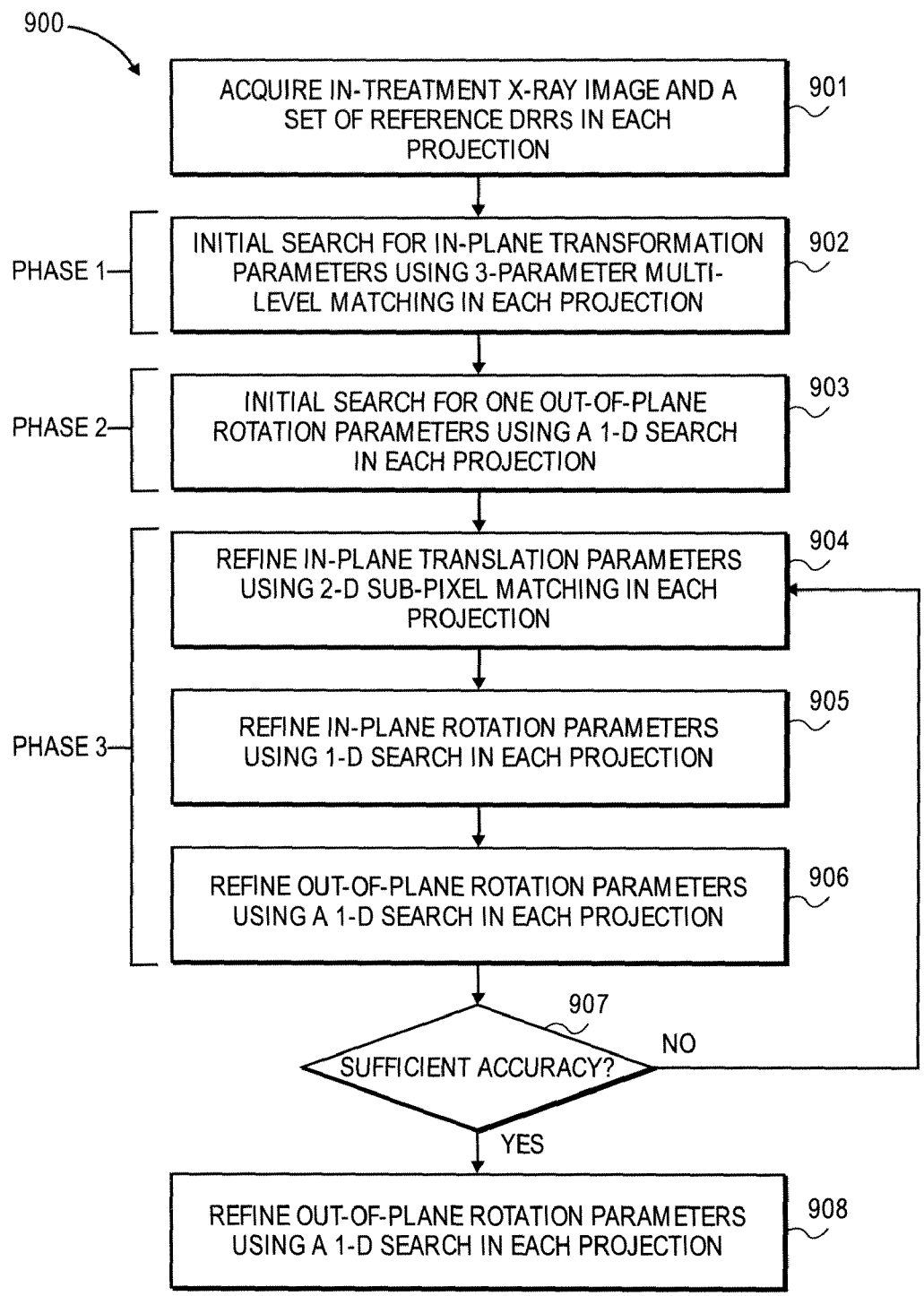
FIG. 9 is a flowchart illustrating another variation of a method of image registration in one embodiment.

FIG. 9 illustrates a second variation 900 of the method of image registration of FIG. 5. The method illustrated in FIG. 9 is identical with the method illustrated in FIG. 8, except that only one out-of-plane rotation is searched in each projection during the initial search, relying on the mapping of one out-of-plane rotation in one projection to an in-plane transformation in the other projection as described above. Thus, in FIG. 9, the method begins with the acquisition of an in-treatment 2-D X-ray and a set of reference DRRs in each projection (e.g., projection A and projection B) (step 901). Next, a first phase of the registration includes an initial search, in each projection, for in-plane transformation parameters using 3-parameter multi-level matching (step 902). Phase 2 of the registration includes an initial search for one out-of-plane rotation parameter in each projection using a 1-D search (step 903). Phase 3 of the registration includes: refinement of the in-plane translation parameters in each projection, using 2-D sub-pixel matching (step 904); refinement of the in-plane rotation parameters in each projection, using 1-D searches (step 905); refinement of the out-of-plane rotation parameter in each projection using a 1-D search (step 906); and checking the accuracy of the in-plane registration result in each projection against a target accuracy (step 907). If, at step 907, the accuracy is insufficient, phase 3 may be repeated. If, at step 906, the accuracy is sufficient, then the out-of-plane rotation parameter may be further refined using a 1-D search in each projection (step 908).

Figure 10:
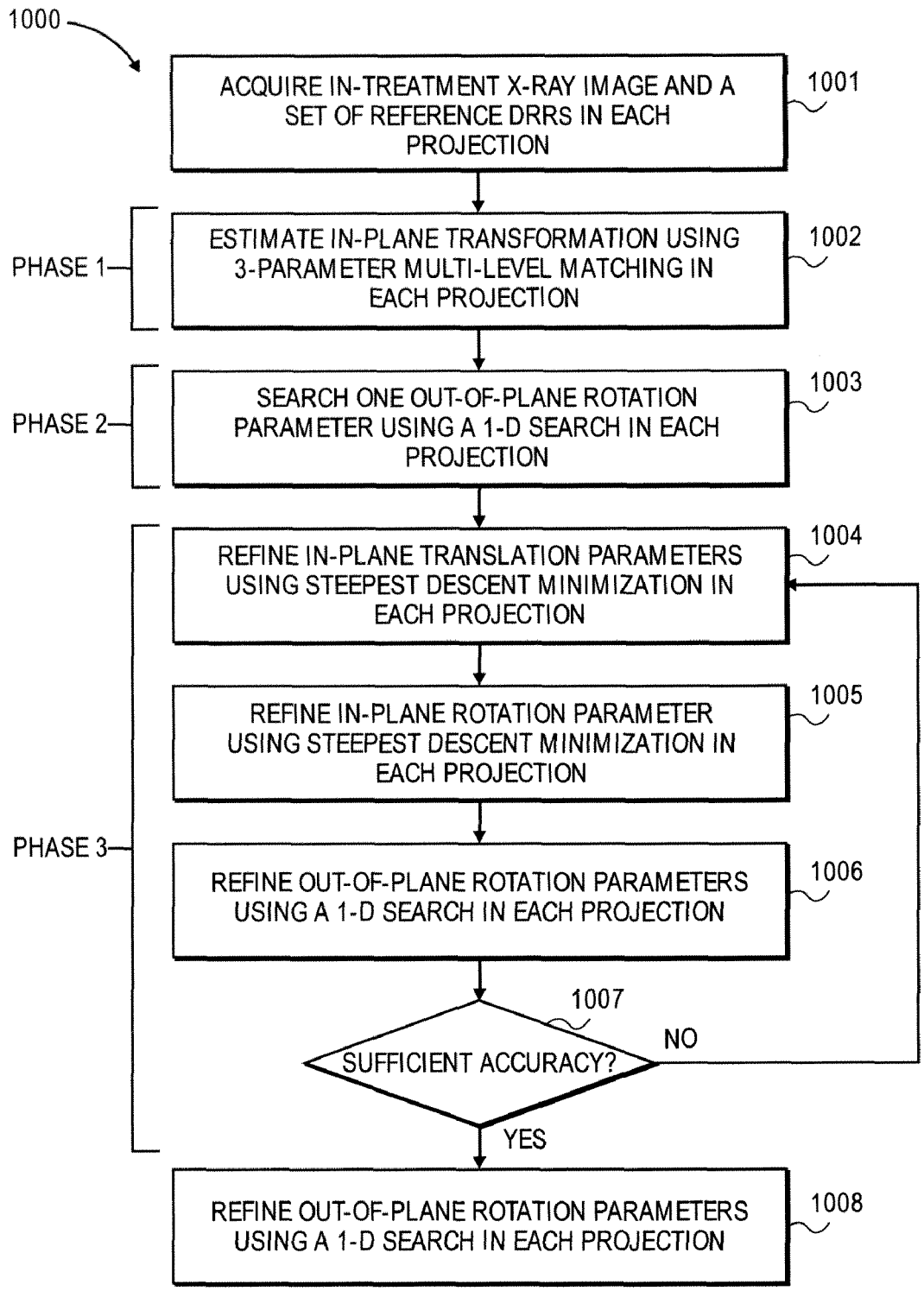
FIG. 10 is a flowchart illustrating still another variation of a method of image registration in one embodiment.

FIG. 10 illustrates a third variation 1000 of the method of image registration of FIG. 5. In FIG. 10, the method begins with the acquisition of an in-treatment 2-D X-ray and a set of reference DRRs in each projection (e.g., projection A and projection B) (step 1001). Next, a first phase of the registration includes estimating, in each projection, in-plane transformation parameters using 3-parameter multi-level matching (step 1002). Phase 2 of the registration includes a search for one out-of-plane rotation parameter in each projection using a 1-D search (step 1003). Phase 3 of the registration includes: refinement of the in-plane translation parameters in each projection, using steepest descent minimization (step 1004); refinement of the in-plane rotation parameters in each projection, using steepest descent minimization (step 1005); refinement of the out-of-plane rotation parameters in each projection, using a 1-D search (step 1006); and checking the accuracy of the in-plane registration result in each projection, against a target accuracy (step 1007). If, at step 1007, the accuracy is insufficient, phase 3 may be repeated. If, at step 1007, the accuracy is sufficient, then the out-of-plane rotation parameters in each projection, may be further refined using a 1-D search employing 1-D interpolation techniques as are known in the art (step 1008).

Figure 11:
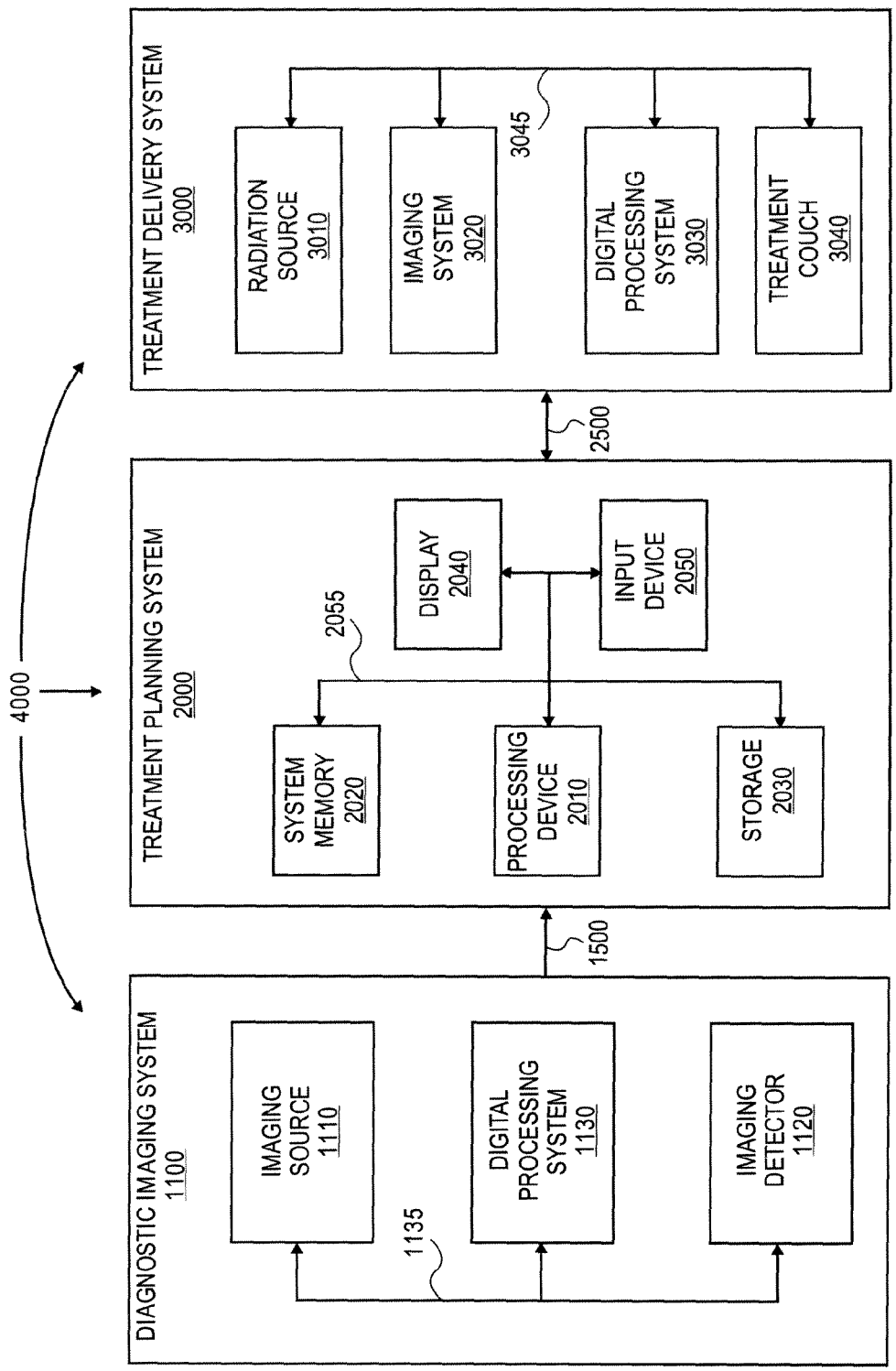
FIG. 11 illustrates a system in which embodiments of the present invention may be practiced.

FIG. 11 illustrates one embodiment of systems that may be used in performing radiation treatment in which features of the present invention may be implemented. As described below and illustrated in FIG. 11, system 4000 may include a diagnostic imaging system 100, a treatment planning system 2000 and a treatment delivery system 3000.

Diagnostic imaging system 1100 may be any system capable of producing medical diagnostic images of a patient that may be used for subsequent medical diagnosis, treatment planning and/or treatment delivery. For example, diagnostic imaging system 1100 may be a computed tomography (CT) system, a magnetic resonance imaging (MRI) system, a positron emission tomography (PET) system, an ultrasound system or the like. For ease of discussion, diagnostic imaging system 1100 may be discussed below at times in relation to a CT x-ray imaging modality. However, other imaging modalities such as those above may also be used.

Diagnostic imaging system 1100 includes an imaging source 1110 to generate an imaging beam (e.g., x-rays, ultrasonic waves, radio frequency waves, etc.) and an imaging detector 1120 to detect and receive the beam generated by imaging source 1110, or a secondary beam or emission stimulated by the beam from the imaging source (e.g., in an MRI or PET scan).

The imaging source 1110 and the imaging detector 1120 may be coupled to a digital processing system 1130 to control the imaging operation and process image data. Diagnostic imaging system 1100 includes a bus or other means 1135 for transferring data and commands among digital processing system 1130, imaging source 1110 and imaging detector 1120. Digital processing system 1130 may include one or more general-purpose processors (e.g., a microprocessor), special purpose processor such as a digital signal processor (DSP) or other type of device such as a controller or field programmable gate array (FPGA). Digital processing system 1130 may also include other components (not shown) such as memory, storage devices, network adapters and the like. Digital processing system 1130 may be configured to generate digital diagnostic images in a standard format, such as the DICOM (Digital Imaging and Communications in Medicine) format, for example. In other embodiments, digital processing system 1130 may generate other standard or non-standard digital image formats. Digital processing system 1130 may transmit diagnostic image files (e.g., the aforementioned DICOM formatted files) to treatment planning system 2000 over a data link 1500, which may be, for example, a direct link, a local area network (LAN) link or a wide area network (WAN) link such as the Internet. In addition, the information transferred between systems may either be pulled or pushed across the communication medium connecting the systems, such as in a remote diagnosis or treatment planning configuration. In remote diagnosis or treatment planning, a user may utilize embodiments of the present invention to diagnose or treatment plan despite the existence of a physical separation between the system user and the patient.

Treatment planning system 2000 includes a processing device 2010 to receive and process image data. Processing device 2010 may represent one or more general-purpose processors (e.g., a microprocessor), special purpose processor such as a digital signal processor (DSP) or other type of device such as a controller or field programmable gate array (FPGA). Processing device 2010 may be configured to execute instructions for performing treatment planning operations discussed herein.

Treatment planning system 2000 may also include system memory 2020 that may include a random access memory (RAM), or other dynamic storage devices, coupled to processing device 2010 by bus 2055, for storing information and instructions to be executed by processing device 2010. System memory 2020 also may be used for storing temporary variables or other intermediate information during execution of instructions by processing device 2010. System memory 2020 may also include a read only memory (ROM) and/or other static storage device coupled to bus 2055 for storing static information and instructions for processing device 2010.

Treatment planning system 2000 may also include storage device 2030, representing one or more storage devices (e.g., a magnetic disk drive or optical disk drive) coupled to bus 2055 for storing information and instructions. Storage device 2030 may be used for storing instructions for performing the treatment planning steps discussed herein.

Processing device 2010 may also be coupled to a display device 2040, such as a cathode ray tube (CRT) or liquid crystal display (LCD), for displaying information (e.g., a 2D or 3D representation of the VOI) to the user. An input device 2050, such as a keyboard, may be coupled to processing device 2010 for communicating information and/or command selections to processing device 2010. One or more other user input devices (e.g., a mouse, a trackball or cursor direction keys) may also be used to communicate directional information, to select commands for processing device 2010 and to control cursor movements on display 2040.

It will be appreciated that treatment planning system 2000 represents only one example of a treatment planning system, which may have many different configurations and architectures, which may include more components or fewer components than treatment planning system 2000 and which may be employed with the present invention. For example, some systems often have multiple buses, such as a peripheral bus, a dedicated cache bus, etc. The treatment planning system 2000 may also include MIRIT (Medical Image Review and Import Tool) to support DICOM import (so images can be fused and targets delineated on different systems and then imported into the treatment planning system for planning and dose calculations), expanded image fusion capabilities that allow the user to treatment plan and view dose distributions on any one of various imaging modalities (e.g., MRI, CT, PET, etc.). Treatment planning systems are known in the art; accordingly, a more detailed discussion is not provided.

Treatment planning system 2000 may share its database (e.g., data stored in storage device 2030) with a treatment delivery system, such as treatment delivery system 3000, so that it may not be necessary to export from the treatment planning system prior to treatment delivery. Treatment planning system 2000 may be linked to treatment delivery system 3000 via a data link 2500, which may be a direct link, a LAN link or a WAN link as discussed above with respect to data link 1500. It should be noted that when data links 1500 and 2500 are implemented as LAN or WAN connections, any of diagnostic imaging system 1100, treatment planning system 2000 and/or treatment delivery system 3000 may be in decentralized locations such that the systems may be physically remote from each other. Alternatively, any of diagnostic imaging system 1100, treatment planning system 2000 and/or treatment delivery system 3000 may be integrated with each other in one or more systems.

Treatment delivery system 3000 includes a therapeutic and/or surgical radiation source 3010 to administer a prescribed radiation dose to a target volume in conformance with a treatment plan. Treatment delivery system 3000 may also include an imaging system 3020 to capture intra-treatment images of a patient volume (including the target volume) for registration or correlation with the diagnostic images described above in order to position the patient with respect to the radiation source. Imaging system 3020 may include any of the imaging systems described above. Treatment delivery system 3000 may also include a digital processing system 3030 to control radiation source 3010, imaging system 3020 and a patient support device such as a treatment couch 3040. Digital processing system 3030 may be configured to register 2-D radiographic images from imaging system 3020, from two or more stereoscopic projections, with digitally reconstructed radiographs (DRRs) generated by digital processing system 1130 in diagnostic imaging system 1100 and/or DRRs generated by processing device 2010 in treatment planning system 2000. Digital processing system 3030 may include one or more general-purpose processors (e.g., a microprocessor), special purpose processor such as a digital signal processor (DSP) or other type of device such as a controller or field programmable gate array (FPGA). Digital processing system 3030 may also include other components (not shown) such as memory, storage devices, network adapters and the like. Digital processing system 3030 may be coupled to radiation source 3010, imaging system 3020 and treatment couch 3040 by a bus 3045 or other type of control and communication interface.

Digital processing system 3030 may implement methods (e.g., such as methods 400, 500, 600, 800, 900 and 1000 described above) to register images obtained from imaging system 3020 with pre-operative treatment planning images in order to align the patient on the treatment couch 3040 within the treatment delivery system 3000, and to precisely position the radiation source with respect to the target volume.

The treatment couch 3040 may be coupled to another robotic arm (not illustrated) having multiple (e.g., 5 or more) degrees of freedom. The couch arm may have five rotational degrees of freedom and one substantially vertical, linear degree of freedom. Alternatively, the couch arm may have six rotational degrees of freedom and one substantially vertical, linear degree of freedom or at least four rotational degrees of freedom. The couch arm may be vertically mounted to a column or wall, or horizontally mounted to pedestal, floor, or ceiling. Alternatively, the treatment couch 3040 may be a component of another mechanical mechanism, such as the Axum® treatment couch developed by Accuray, Inc. of California, or be another type of conventional treatment table known to those of ordinary skill in the art.

It should be noted that the methods and apparatus described herein are not limited to use only with medical diagnostic imaging and treatment. In alternative embodiments, the methods and apparatus herein may be used in applications outside of the medical technology field, such as industrial imaging and non-destructive testing of materials (e.g., motor blocks in the automotive industry, airframes in the aviation industry, welds in the construction industry and drill cores in the petroleum industry) and seismic surveying.

In such applications, for example, "treatment" may refer generally to the application of radiation beam(s).

It will be apparent from the foregoing description that aspects of the present invention may be embodied, at least in part, in software. That is, the techniques may be carried out in a computer system or other data processing system in response to its processor, such as processing device 2010, for example, executing sequences of instructions contained in a memory, such as system memory 2020, for example. In various embodiments, hardware circuitry may be used in combination with software instructions to implement the present invention. Thus, the techniques are not limited to any specific combination of hardware circuitry and software or to any particular source for the instructions executed by the data processing system. In addition, throughout this description, various functions and operations may be described as being performed by or caused by software code to simplify description. However, those skilled in the art will recognize what is meant by such expressions is that the functions result from execution of the code by a processor or controller, such as processing device 2010.

A machine-readable medium can be used to store software and data which when executed by a data processing system causes the system to perform various methods of the present invention. This executable software and data may be stored in various places including, for example, system memory 2020 and storage 2030 or any other device that is capable of storing software programs and/or data.

Thus, a machine-readable medium includes any mechanism that provides (i.e., stores and/or transmits) information in a form accessible by a machine (e.g., a computer, network device, personal digital assistant, manufacturing tool, any device with a set of one or more processors, etc.). For example, a machine-readable medium includes recordable/non-recordable media (e.g., read only memory (ROM); random access memory (RAM); magnetic disk storage media; optical storage media; flash memory devices; etc.), as well as electrical, optical, acoustical or other forms of propagated signals (e.g., carrier waves, infrared signals, digital signals, etc.); etc.

It should be appreciated that references throughout this specification to "one embodiment" or "an embodiment" means that a particular feature, structure or characteristic described in connection with the embodiment is included in at least one embodiment of the present invention. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the invention. In addition, while the invention has been described in terms of several embodiments, those skilled in the art will recognize that the invention is not limited to the embodiments described. The embodiments of the invention can be practiced with modification and alteration within the scope of the appended claims. The specification and the drawings are thus to be regarded as illustrative instead of limiting on the invention.

What is claimed is:

1. A method, comprising:
   estimating, by a processing device, transformation parameters between a 2-D projection of a volume and a 2-D reference image of the volume in a plurality of search-phases, the estimating comprising:

estimating in-plane transformation parameters between the 2-D projection of the volume and a 2-D reference image generated from 3-D scan data of the volume in a first search-phase; and estimating out-of-plane rotation parameters between the 2-D projection and a plurality of 2-D reference images generated from the 3-D scan data of the volume in a second search-phase; and searching, by the processing device, for 2-D transformation parameters in each of the plurality of search-phases using combinations of search techniques and similarity measures in each search-phase.

2. The method of claim 1, further comprising:

repeating a search for one or more transformation parameters to achieve a desired registration accuracy between the 2-D projection of the volume and the 2-D reference image of the volume.

3. The method of claim 2, wherein estimating the transformation parameters between the 2-D projection of the volume and the 2-D reference image of the volume comprises: estimating the in-plane transformation parameters between the 2-D projection of the volume and a 2-D reference image generated from 3-D scan data of the volume, using a first similarity measure and a first search method in each of two or more projections; and estimating the out-of-plane rotation parameters between the 2-D projection and a plurality of 2-D reference images generated from the 3-D scan data of the volume, using a second similarity measure and a second search method in each of the two or more projections.

4. The method of claim 3, wherein repeating a search for one or more transformation parameters to achieve a desired registration accuracy between the 2-D projection of the volume and the 2-D reference image of the volume comprises refining the in-plane transformation parameters and the out-of-plane rotation parameters using the second similarity measure and at least a third search method in each of the two or more projections.

5. The method of claim 4, wherein the out-of-plane rotation parameters in each of the two or more projections comprise two out-of-plane rotation parameters, and wherein the second search method comprises a 1-D search in each of the two or more projections.

6. The method of claim 5, wherein the 1-D search searches the two out-of-plane rotation parameters in each of the two or more projections.

7. The method of claim 5, wherein one of the out-of-plane rotation parameters in each projection comprises one of the in-plane rotation parameters in another projection, and wherein the 1-D search searches only one of the two out-of-plane rotation parameters in each of the two or more projections.

8. The method of claim 5, wherein the in-plane transformation parameters comprise two in-plane translations and one in-plane rotation in each projection, wherein the second similarity measure comprises an optimized pattern intensity similarity measure, and wherein refining the in-plane transformation parameters in each projection comprises: refining the in-plane translation parameters in each projection using 2-D sub-pixel matching; and refining the in-plane rotation parameter in each projection using the 1-D search.

9. The method of claim 8, further comprising: determining whether the in-plane translation parameters and the in-plane rotation parameters in each projection have enough accuracy to achieve a desired registration accuracy; and repeating the method of claim 8 if the in-plane translation parameters and the in-plane rotation parameters do not have enough accuracy to achieve the desired registration accuracy; else refining the out-of-plane rotation parameters in each projection using the 1-D search.

10. The method of claim 5, wherein the in-plane transformation parameters comprise two in-plane translations and one in-plane rotation in each projection, wherein the second similarity measure comprises an optimized pattern intensity similarity measure, and wherein refining the in-plane transformation parameters and the out-of-plane rotation parameters comprises: refining the in-plane translation parameters in each projection using a steepest descent minimization; refining the in-plane rotation parameters in each projection using the steepest descent minimization; and refining the out-of-plane rotation parameters in each projection using the 1-D search.

11. The method of claim 10, further comprising: determining whether the in-plane translation parameters and the in-plane rotation parameters in each projection have enough accuracy to achieve a desired registration accuracy; and repeating the method of claim 10 if the in-plane translation parameters and the in-plane rotation parameters do not have enough accuracy to achieve the desired registration accuracy; else refining the out-of-plane rotation parameters in each projection using the 1-D search.

12. The method of claim 3, wherein the first similarity measure comprises a simple similarity measure and the first search method comprises a hierarchical search.

13. The method of claim 12, wherein the hierarchical search comprises 3-parameter multi-level matching.

14. The method of claim 12, wherein the first similarity measure is one of a sum of squared differences (SSD) measure and a sum of absolute differences (SAD) measure.

15. The method of claim 1, further comprising converting the transformation parameters into a 3-D rigid transformation of the volume.

16. An article of manufacture, including machine-accessible instructions that when accessed by a data processing system, cause the data processing system to perform a method, comprising:

estimating transformation parameters between a 2-D projection of a volume and a 2-D reference image of the volume in a plurality of search-phases, the estimating comprising:

estimating in-plane transformation parameters between the 2-D projection of the volume and a 2-D reference image generated from 3-D scan data of the volume in a first search-phase; and estimating out-of-plane rotation parameters between the 2-D projection and a plurality of 2-D reference images generated from the 3-D scan data of the volume in a second search-phase; and searching for 2-D transformation parameters in each of the plurality of search-phases using combinations of search techniques and similarity measures in each search phase.

17. The article of manufacture of claim 16, further comprising repeating a search for one or more transformation parameters to achieve a desired registration accuracy between the 2-D projection of the volume and the 2-D reference image of the volume.

18. The article of manufacture of claim 17, wherein estimating the transformation parameters between the 2-D projection of the volume and the 2-D reference image of the volume comprises:

estimating the in-plane transformation parameters between the 2-D projection of the volume and a 2-D reference image generated from 3-D scan data of the volume, using a first similarity measure and a first search method in each of two or more projections; and estimating the out-of-plane rotation parameters between the 2-D projection and a plurality of 2-D reference images generated from the 3-D scan data of the volume, using a second similarity measure and a second search method in each of the two or more projections.

19. The article of manufacture of claim 18, the method further comprising refining the in-plane transformation parameters and the out-of-plane rotation parameters using the second similarity measure and at least a third search method in each of the two or more projections.

20. The article of manufacture of claim 19, wherein the out-of-plane rotation parameters in each of the two or more projections comprise two out-of-plane rotation parameters, and wherein the second search method comprises a 1-D search in each of the two or more projections.

21. The article of manufacture of claim 20, wherein the 1-D search searches the two out-of-plane rotation parameters in each of the two or more projections.

22. The article of manufacture of claim 20, wherein one of the out-of-plane rotation parameters in each projection comprises one of the in-plane rotation parameters in another projection, and wherein the 1-D search searches only one of the two out-of-plane rotation parameters in each of the two or more projections.

23. The article of manufacture of claim 20, wherein the in-plane transformation parameters comprise two in-plane translations and one in-plane rotation in each projection, wherein the second similarity measure comprises an optimized pattern intensity similarity measure, and wherein refining the in-plane transformation parameters in each projection comprises: refining the in-plane translation parameters in each projection using 2-D sub-pixel matching and; and refining the in-plane rotation parameter in each projection using the 1-D search.

24. The article of manufacture of claim 23, the method further comprising: determining whether the in-plane translation parameters and the in-plane rotation parameters in each projection have enough accuracy to achieve a desired registration accuracy; and repeating the method of claim 23 if the in-plane translation parameters and the in-plane rotation parameters do not have enough accuracy to achieve the desired registration accuracy; else refining the out-of-plane rotation parameters in each projection using the 1-D search.

25. The article of manufacture of claim 20, wherein the in-plane transformation parameters comprise two in-plane translations and one in-plane rotation in each projection, wherein the second similarity measure comprises an optimized pattern intensity similarity measure, and wherein refining the in-plane transformation parameters and the out-of-plane rotation parameters comprises: refining the in-plane translation parameters in each projection using a steepest descent minimization; refining the in-plane rotation parameters in each projection using the steepest descent minimization; and refining the out-of-plane rotation parameters in each projection using the 1-D search.

26. The article of manufacture of claim 25, the method further comprising: determining whether the in-plane translation parameters and the in-plane rotation parameters in each projection have enough accuracy to achieve a desired registration accuracy; and repeating the method of claim 25 if the in-plane translation parameters and the in-plane rotation parameters do not have enough accuracy to achieve the desired registration accuracy; else refining the out-of-plane rotation parameters in each projection using the 1-D search.

27. The article of manufacture of claim 18, wherein the first similarity measure comprises a SSD similarity measure and the first search method comprises a hierarchical search.

28. The article of manufacture of claim 27, wherein the hierarchical search comprises 3-parameter multi-level matching.

29. The article of manufacture of claim 27, wherein the first similarity measure is one of a sum of squared differences (SSD) measure and a sum of absolute differences (SAD) measure.

30. The article of manufacture of claim 16, the method further comprising converting the transformation parameters into a 3-D rigid transformation of the volume.

31. A system comprising a processing device, wherein the processing device is configured to estimate transformation parameters between a 2-D projection of a volume and a 2-D reference image of the volume in a plurality of search-phases, wherein to estimate the transformation parameters between the 2-D projection of the volume and the 2-D reference image of the volume, the processing device is configured to estimate in-plane transformation parameters between the 2-D projection of the volume and a 2-D reference image generated from 3-D scan data of the volume in a first search-phase and estimate out-of-plane rotation parameters between the 2-D projection and a plurality of 2-D reference images generated from the 3-D scan data of the volume in a second search-phase, and wherein the processing device is further configured to search for 2-D transformation parameters in each of the plurality of search-phases using combinations of search techniques and similarity measures in each search phase.

32. The system of claim 31, wherein the processing device is further configured to repeat a search for one or more transformation parameters to achieve a desired registration accuracy between the 2-D projection of the volume and the 2-D reference image of the volume.

33. The system of claim 32, wherein to estimate the transformation parameters between the 2-D projection of the volume and the 2-D reference image of the volume, the processing device is configured to estimate the in-plane transformation parameters between the 2-D projection of the volume and the 2-D reference image generated from the 3-D scan data of the volume, using a first similarity measure and a first search method in each of two or more projections, and wherein the processing device is further configured to estimate the out-of-plane rotation parameters between the 2-D projection and the plurality of 2-D reference images using a second similarity measure and a second search method in each of the two or more projections.

34. The system of claim 33, further comprising a data storage device coupled with the data processing device to store a plurality of 2-D projections of the volume and a plurality of 2-D reference images generated from 3-D scan data of the volume.

35. The system of claim 34, wherein the processing device is further configures to refine the in-plane transformation parameters and the out-of-plane rotation parameters using a second similarity measure and at least a third search method in each of the two or more projections.

36. The system of claim 35, wherein the out-of-plane rotation parameters in each of the two or more projections comprise two out-of-plane rotation parameters, and wherein the second search method comprises a 1-D search in each of the two or more projections.

37. The system of claim 36, wherein the 1-D search searches the two out-of-plane rotation parameters in each of the two or more projections.

38. The system of claim 36, wherein one of the out-of-plane rotation parameters in each projection comprises one of the in-plane rotation parameters in another projection, and wherein the 1-D search searches only one of the two out-of-plane rotation parameters in each of the two or more projections.

39. The system of claim 36, wherein the in-plane transformation parameters comprise two in-plane translations and one in-plane rotation in each projection, wherein the second similarity measure comprises an optimized pattern intensity similarity measure, and wherein to refine the in-plane transformation parameters in each projection, the processing device is further configured to refine the in-plane translation parameters in each projection using 2-D sub-pixel matching and to refine the in-plane rotation parameter in each projection using the 1-D search.

40. The system of claim 39, wherein the processing device is further configured to determine whether the in-plane translation parameters and the in-plane rotation parameters in each projection have enough accuracy to achieve a desired registration accuracy, to further refine the in-plane transformation parameters in each projection if the in-plane translation parameters and the in-plane rotation parameters do not have enough accuracy to achieve the desired registration accuracy, else to refine the out-of-plane rotation parameters in each projection using the 1-D search.

41. The system of claim 36, wherein the in-plane transformation parameters comprise two in-plane translations and one in-plane rotation in each projection, wherein the second similarity measure comprises an optimized pattern intensity similarity measure, and wherein to refine the in-plane transformation parameters and the out-of-plane rotation parameters the processing device is further configured to refine the in-plane translation parameters in each projection using a steepest descent minimization, to refine the in-plane rotation parameters in each projection using the steepest descent minimization, and to refine the out-of-plane rotation parameters in each projection using the 1-D search.

42. The system of claim 41, wherein the processing device is further configured to determine whether the in-plane translation parameters and the in-plane rotation parameters in each projection have enough accuracy to achieve a desired registration accuracy, and to further to refine the in-plane transformation parameters and the out-of-plane rotation parameters if the in-plane translation parameters and the in-plane rotation parameters do not have enough accuracy to achieve the desired registration accuracy, else to refine the out-of-plane rotation parameters in each projection using the 1-D search.

43. The system of claim 34, wherein the first similarity measure comprises a SSD similarity measure and the first search method comprises a hierarchical search.

44. The system of claim 43, wherein the hierarchical search comprises 3-parameter multi-level matching.

45. The system of claim 43, wherein the first similarity measure is one of a sum of squared differences (SSD) measure and a sum of absolute differences (SAD) measure.

46. The system of claim 34, wherein the second similarity measure comprises an optimized pattern intensity similarity measure.

47. The system of claim 34, further comprising: an imaging system coupled with the data storage device to generate the plurality of 2-D projection of the volume; and a treatment planning system to generate the plurality of 2-D reference images from the 3-D scan data of the volume, the plurality of 2-D reference images comprising a nominal in-plane reference image and a plurality of out-of-plane reference images in each of the two or more projections.

48. The system of claim 31, wherein the processing device is further configured to convert the transformation parameters into a 3-D rigid transformation of the volume.

49. An apparatus, comprising:
means for estimating transformation parameters between a 2-D projection of a volume and a 2-D reference image of the volume in a plurality of search-phases, the estimating comprising:
estimating in-plane transformation parameters between the 2-D projection of the volume and a 2-D reference image generated from 3-D scan data of the volume in a first search-phase; and
estimating out-of-plane rotation parameters between the 2-D projection and a plurality of 2-D reference images generated from the 3-D scan data of the volume in a second search-phase; and
means for searching for 2-D transformation parameters in each of the plurality of search-phases using combinations of search techniques and similarity measures in each search phase.

50. The apparatus of claim 49, further comprising means for repeating a search for one or more transformation parameters to achieve a desired registration accuracy between the 2-D projection of the volume and the 2-D reference image of the volume.

51. The apparatus of claim 50, further comprising means for converting the transformation parameters into a 3-D rigid transformation of the volume.

* * * * *